(12) United States Patent
Alajem et al.

(10) Patent No.: US 6,887,662 B1
(45) Date of Patent: May 3, 2005

(54) OLIGONUCLEOTIDES AND ASSEMBLIES THEREOF USEFUL IN THE DETECTION OF THE PRESENCE OR ABSENCE OF TARGET NUCLEIC ACID SEQUENCES IN A SAMPLE

(75) Inventors: Sara Alajem, Kfar Hanagid (IL); Avraham Reinhartz, Gan Yavne (IL); Michal Waksman, Gan Yavne (IL)

(73) Assignee: Diasorin srl, Salvggia (IT)

( * ) Notice: Subject to any disclaimer, the term of this patent is extended or adjusted under 35 U.S.C. 154(b) by 99 days.

(21) Appl. No.: 09/727,480

(22) Filed: Dec. 4, 2000

Related U.S. Application Data

(63) Continuation-in-part of application No. 09/449,545, filed on Nov. 29, 1999, now abandoned.

(51) Int. Cl.[7] ............................ C12Q 1/68; C12P 19/34; C07H 21/02

(52) U.S. Cl. ..................... 435/6; 435/91.1; 435/91.2; 435/91.21; 435/91.5; 536/23.1; 536/24.3; 536/24.31; 536/24.33

(58) Field of Search ..................... 435/6, 91.2, 91.21, 435/91.5; 536/231, 24.3, 24.31, 24.33

(56) References Cited

U.S. PATENT DOCUMENTS

| | | | | |
|---|---|---|---|---|
| 5,118,801 A | * | 6/1992 | Lizardi et al. | 536/27 |
| 5,451,503 A | * | 9/1995 | Hogan et al. | 435/6 |
| 5,925,517 A | * | 7/1999 | Tyagi et al. | 435/6 |

* cited by examiner

*Primary Examiner*—Jeffrey Fredman
(74) *Attorney, Agent, or Firm*—G. E. Ehrlich (1995) Ltd.

(57) ABSTRACT

Oligonucleotides useful in the detection of a nucleic acid target sequence in a sample.

6 Claims, 9 Drawing Sheets

(4 of 9 Drawing Sheet(s) Filed in Color)

| | | | |
|---|---|---|---|
| Paired Probes | ⊥⌐ | | |
| Modified paired probes | SpltRE | MutRE | SBP |
| Bivalent Probes | BIV1 | BIV2 | BIV3 |
| Single Probes | ⊥Ω | | |
| Modified single probes | Looped, set A | Modified looped probes, set B | |
| Blocked Probes | ⊥⌐ → ⊥⌐ | | |

Fig. 2

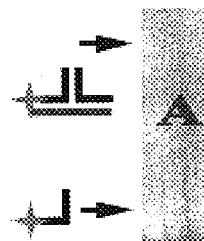 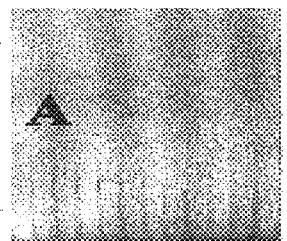 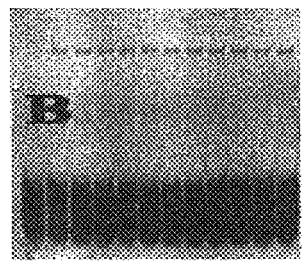 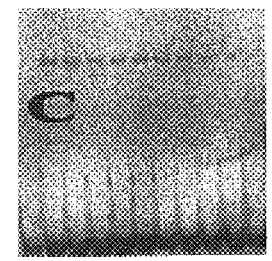
Temp (°C): 46 50 54 58 62 66     46 50 54 58 62 66     46 50 54 58 62 66
Fig. 5a                Fig. 5b                Fig. 5c
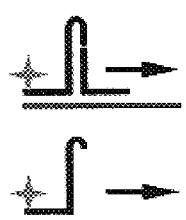 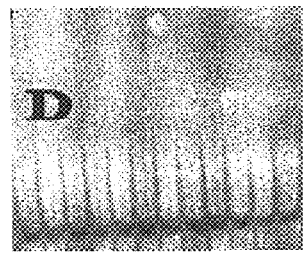 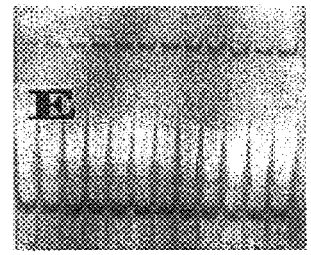
Temp (°C): 64 60 56 52 48 44     64 60 56 52 48 44
Fig. 5d                Fig. 5e

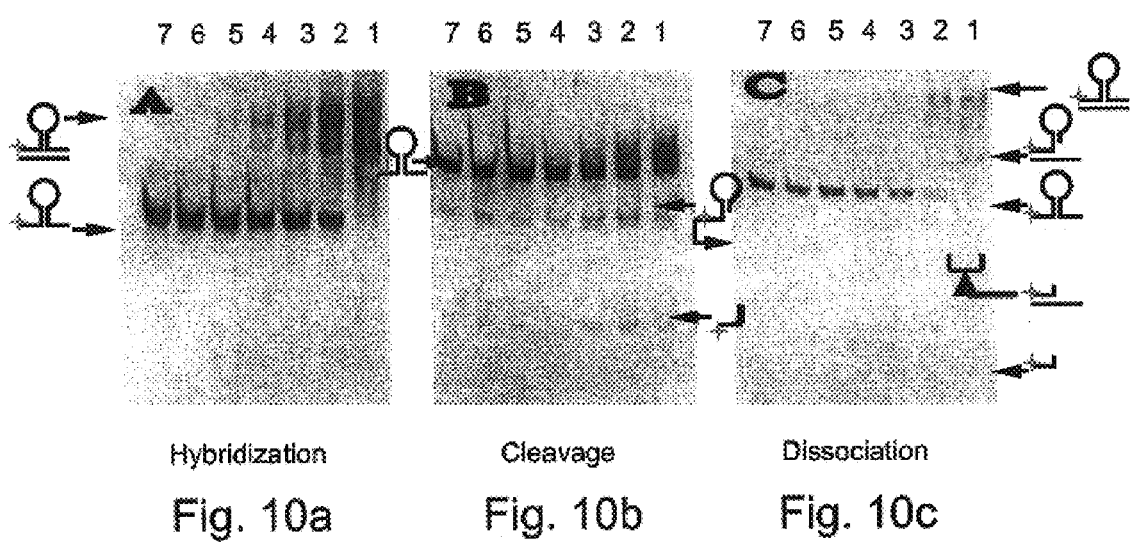
Fig. 10a Hybridization
Fig. 10b Cleavage
Fig. 10c Dissociation

SEQUENCE LISTING

<160> NUMBER OF SEQ ID NOS: 49

<210> SEQ ID NO 1
<211> LENGTH: 263
<212> TYPE: DNA
<213> ORGANISM: Human cytomegalovirus (strain AD169)

<400> SEQUENCE: 1
agaccttcat gcagatctcc tcaatgcggc gcttcattac actgataacc tcaggcttgg      60
ttatcagagg ccgcttggcc agcatcacac tagtctcctc taagacatag cagcacagca     120
cccgacagaa ctcacttaag agagagatgc ccccgtacat ggtcatcata caagcgtcac     180
tagtgacctt gtactcatta cacattgttt ccacacatgt agtgaggata tccataaata     240
tgtgatcaat gtgcgtgagc acc                                             263

<210> SEQ ID NO 2
<211> LENGTH: 20
<212> TYPE: DNA
<213> ORGANISM: Artificial sequence
<220> FEATURE:
<223> OTHER INFORMATION: primer

<400> SEQUENCE: 2
agaccttcat gcagatctcc                                                  20

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
ggtgctcacg cacattgatc                                                  20

<210> SEQ ID NO 4
<211> LENGTH: 263
<212> TYPE: DNA
<213> ORGANISM: Human cytomegalovirus (strain AD169)
<220> FEATURE:
<223> OTHER INFORMATION: antisense

<400> SEQUENCE: 4

```
ggtgctcacg cacattgatc acatatttat ggatatcctc actacatgtg tggaaacaat    60
gtgtaatgag tacaaggtca ctagtgacgc ttgtatgatg accatgtacg ggggcatctc   120
tctcttaagt gagttctgtc gggtgctgtg ctgctatgtc ttagaggaga ctagtgtgat   180
gctggccaag cggcctctga taaccaagcc tgaggttatc agtgtaatga agcgccgcat   240
tgaggagatc tgcatgaagg tct                                          263
```

<210> SEQ ID NO 5
<211> LENGTH: 50
<212> TYPE: DNA
<213> ORGANISM: Human cytomegalovirus (strain AD169)

<400> SEQUENCE: 5

```
tcaggcttgg ttatcagagg ccgcttggcc agcatcacac tagtctcctc              50
```

<210> SEQ ID NO 6
<211> LENGTH: 35
<212> TYPE: DNA
<213> ORGANISM: Human cytomegalovirus (strain AD169)

<400> SEQUENCE: 6

```
ggccagcatc acactagtct cctctaagac atagc                              35
```

<210> SEQ ID NO 7
<211> LENGTH: 59
<212> TYPE: DNA
<213> ORGANISM: Human cytomegalovirus (strain AD169)

<400> SEQUENCE: 7

```
ggccagcatc acactagtct cctctaagac atagcagcac agcaccccgac agaactcac    59
```

<210> SEQ ID NO 8
<211> LENGTH: 36
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 8

```
cagcatcaca ctagtctcct ctaagacata gcagca                             36
```

<210> SEQ ID NO 9
<211> LENGTH: 36
<212> TYPE: DNA
<213> ORGANISM: Artificial sequence
<220> FEATURE:
<223> OTHER INFORMATION: synthetic oligonucleotide

<400> SEQUENCE: 9

```
tgctgctatg tcttagagga gactagtgtg atgctg                             36
```

<210> SEQ ID NO 10
<211> LENGTH: 36
<212> TYPE: DNA
<213> ORGANISM: Artificial sequence
<220> FEATURE:
<223> OTHER INFORMATION: hybridized oligonucleotides
<220> FEATURE:
<221> NAME/KEY: misc_feature
<222> LOCATION: (1)..(1)
<223> OTHER INFORMATION: Biotinylated at 5'-end of sense

<400> SEQUENCE: 10
cagcatcaca ctagtctcct ctaagacata gcagca                                   36

<210> SEQ ID NO 11
<211> LENGTH: 37
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 11
tggttatcag aggccgctta aaattcgaag ggttcac                                  37

<210> SEQ ID NO 12
<211> LENGTH: 37
<212> TYPE: DNA
<213> ORGANISM: Artificial sequence
<220> FEATURE:
<223> OTHER INFORMATION: synthetic oligonucleotide

<400> SEQUENCE: 12
gtgaaccctt cgaattcaca gcatcacact agtctcc                                  37

<210> SEQ ID NO 13
<211> LENGTH: 32
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 13
tggttatcag aggccgctta aaattcgaag gg                                       32

<210> SEQ ID NO 14
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 14
cccttcgaat tcacagcatc acactagtct cc                                       32

<210> SEQ ID NO 15
<211> LENGTH: 36
<212> TYPE: DNA
<213> ORGANISM: Artificial sequence
<220> FEATURE:
<223> OTHER INFORMATION: synthetic oligonucleotide
<220> FEATURE:

-continued

```
<221> NAME/KEY: misc_feature
<222> LOCATION: (1)..(1)
<223> OTHER INFORMATION: Biotinylated at 5'-end

<400> SEQUENCE: 15
ggcttggtta tcagaggccg cttaaaattc gaaggg                                36

<210> SEQ ID NO 16
<211> LENGTH: 37
<212> TYPE: DNA
<213> ORGANISM: Artificial sequence
<220> FEATURE:
<223> OTHER INFORMATION: synthetic oligonucleotide

<400> SEQUENCE: 16
cccttcgaat tcacagcatc acactagtct cctctaa                               37

<210> SEQ ID NO 17
<211> LENGTH: 39
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 17
tggttatcag aggccgctta aaattcgaag ggttcacga                             39

<210> SEQ ID NO 18
<211> LENGTH: 39
<212> TYPE: DNA
<213> ORGANISM: Artificial sequence
<220> FEATURE:
<223> OTHER INFORMATION: synthetic oligonucleotide

<400> SEQUENCE: 18
tcgtgaaccc ttcgaattca cagcatcaca ctagtctcc                             39

<210> SEQ ID NO 19
<211> LENGTH: 43
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 19
cagcatcaca ctagtctcca gctagttcga cgcgccacgc gtc                        43

<210> SEQ ID NO 20
<211> LENGTH: 53
<212> TYPE: DNA
<213> ORGANISM: Artificial sequence
<220> FEATURE:
<223> OTHER INFORMATION: synthetic oligonucleotide

<400> SEQUENCE: 20
gaactagcta ctctaagaca tagcagcaca gcacccgaca gaactcactt aag             53

<210> SEQ ID NO 21
<211> LENGTH: 24
```

```
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end
<220> FEATURE:
<221> NAME/KEY: modified_base
<222> LOCATION: (20)..(20)
<223> OTHER INFORMATION: m6a

<400> SEQUENCE: 21
gtacgggggc ataaattcga acgc                                          24

<210> SEQ ID NO 22
<211> LENGTH: 24
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 22
gtacgggggc ataaattcga acgc                                          24

<210> SEQ ID NO 23
<211> LENGTH: 38
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 23
tttttttttg cgttcgaatt tctctctctt aagtgagt                           38

<210> SEQ ID NO 24
<211> LENGTH: 52
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 24
tcactagtga cgcttgtatg atgaccatgt acgggggcat aaattcgaac gc           52

<210> SEQ ID NO 25
<211> LENGTH: 52
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end
<220> FEATURE:
<221> NAME/KEY: modified_base
<222> LOCATION: (48)..(48)
```

<223> OTHER INFORMATION: m6a

<400> SEQUENCE: 25
tcactagtga cgcttgtatg atgaccatgt acgggggcat aaattcgaac gc      52

<210> SEQ ID NO 26
<211> LENGTH: 64
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 26
ttatcagagg ccgcttgaaa attcgaattg accaagaatt cgaattcaca gcatcacact      60
agtc      64

<210> SEQ ID NO 27
<211> LENGTH: 65
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 27
gttatcagag gccacttgaa aattcgaatt gaccaagaat tcgaattcac agcatcacac      60
tagtc      65

<210> SEQ ID NO 28
<211> LENGTH: 83
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 28
tggttatcag aggccgcttg ttataatcga ataaatggag gaagattaat tcgaatataa      60
gccagcatca cactagtctc ctc      83

<210> SEQ ID NO 29
<211> LENGTH: 89
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 29
tggttatcag aggccgcttg ttatattcga ataaatgacc gaggaggaag attaattcga      60
atataagcca gcatcacact agtctcctc      89

```
<210> SEQ ID NO 30
<211> LENGTH: 77
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 30
cagcatcaca ctagtctcta ctcgagcaaa aaaaaaaaaa aaaaaaaac actcgagcgc      60 tctaagacat agcagca                                                   77

<210> SEQ ID NO 31
<211> LENGTH: 68
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 31
cagcatcaca ctagtctcta cacacacatc gagcattcga cacacacacg ctctaagaca     60
tagcagca                                                             68

<210> SEQ ID NO 32
<211> LENGTH: 77
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 32
cagcatcaca ctagtctcta cactcgagca cacaaaaaaa aaaaacacac tcgagcacgc     60
tctaagacat agcagca                                                   77

<210> SEQ ID NO 33
<211> LENGTH: 77
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 33
cagcatcaca ctagtctcta ctcgagcaca cacaaaaaaa aaaaacacac actcgagcgc     60
tctaagacat agcagca                                                   77

<210> SEQ ID NO 34
<211> LENGTH: 87
<212> TYPE: DNA
<213> ORGANISM: Artificial sequence
<220> FEATURE:
<223> OTHER INFORMATION: synthetic oligonucleotide
<220> FEATURE:
```

```
<221> NAME/KEY: misc_feature
<222> LOCATION: (1)..(1)
<223> OTHER INFORMATION: Biotinylated at 5'-end

<400> SEQUENCE: 34
cagcatcaca ctagtctcta cacacctcga gcaaaaaaaa aaaaaaaaaa aaaacactcg      60
agacacacgc tctaagacat agcagca                                          87

<210> SEQ ID NO 35
<211> LENGTH: 81
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 35
cagcatcaca ctagtctcta cactcgagca cacaaaaaaa aaaaaaaaac acactcgagc      60
acgctctaag acatagcagc a                                                81

<210> SEQ ID NO 36
<211> LENGTH: 54
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 36
gccagcatca cactaccccc tcgaggattc gaaaaaacct ctaagacata gcag            54

<210> SEQ ID NO 37
<211> LENGTH: 58
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 37
cagcatcaca ctagtcactc gaggagaccc gtgtcgaacc tcctctaaga catagcag        58

<210> SEQ ID NO 38
<211> LENGTH: 60
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 38
gaactcactt aagagagaga tgcccccgta catggtcatc atacaagcgt cactagtgac      60

<210> SEQ ID NO 39
<211> LENGTH: 44
```

```
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 39
cagcatcaca ctagtctcaa ttcgaagcgg atgaccatgt acgg                44

<210> SEQ ID NO 40
<211> LENGTH: 47
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 40
cactagtgac gcttgtatcg cttcgaattc tctaagacat agcagca             47

<210> SEQ ID NO 41
<211> LENGTH: 50
<212> TYPE: DNA
<213> ORGANISM: Human cytomegalovirus (strain AD169)

<400> SEQUENCE: 41
tcaggcttgg ttatcagagg ccgcttggcc agcatcacac tagtctcctc          50

<210> SEQ ID NO 42
<211> LENGTH: 59
<212> TYPE: DNA
<213> ORGANISM: Artificial sequence
<220> FEATURE:
<223> OTHER INFORMATION: synthetic oligonucleotide

<400> SEQUENCE: 42
atgtgtggaa acaatgtgta atgagtacaa ggtcactagt gacgcttgta tgatgacca    59

<210> SEQ ID NO 43
<211> LENGTH: 41
<212> TYPE: DNA
<213> ORGANISM: Artificial sequence
<220> FEATURE:
<223> OTHER INFORMATION: synthetic oligonucleotide

<400> SEQUENCE: 43
cgaatttgac cttgtactca ttacacattg tttccacaca t                   41

<210> SEQ ID NO 44
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 44
cgaatttgac cttgtactca ttacacat                                  28

<210> SEQ ID NO 45
<211> LENGTH: 47
<212> TYPE: DNA
```

```
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 45
tggtcatcat acaagcgtca ctagaattcg aacggttttt ttccgtt                    47

<210> SEQ ID NO 46
<211> LENGTH: 43
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 46
catcatacaa gcgtcactag aattcgaacg gttttttttcc gtt                       43

<210> SEQ ID NO 47
<211> LENGTH: 39
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 47
atacaagcgt cactagaatt cgaacggttt ttttccgtt                             39

<210> SEQ ID NO 48
<211> LENGTH: 59
<212> TYPE: DNA
<213> ORGANISM: Artificial sequence
<220> FEATURE:
<223> OTHER INFORMATION: synthetic oligonucleotide

<400> SEQUENCE: 48
atgtgtggaa acaatgtgta atgagtacaa ggtcagtagt gacgcttgta tgatgacca      59

<210> SEQ ID NO 49
<211> LENGTH: 27
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: Biotinylated at 5'-end

<400> SEQUENCE: 49
tttcatcata aaagcgtcac tagaatt                                          27
```

OLIGONUCLEOTIDES AND ASSEMBLIES THEREOF USEFUL IN THE DETECTION OF THE PRESENCE OR ABSENCE OF TARGET NUCLEIC ACID SEQUENCES IN A SAMPLE

This is a continuation-in-part of U.S. patent application Ser. No. 09/449,545, filed Nov. 29, 1999 now abandoned.

FIELD AND BACKGROUND OF THE INVENTION

The present invention relates to oligonucleotide probes and methods for the detection of target nucleic acid sequences in a sample. More particularly, the present invention relates to oligonucleotide probes which are internally cleavable when hybridized to target nucleic acid sequences, such cleavage leading to both signal generation and amplification by recycling.

The identification of a target nucleic acid sequence is of great importance in both biological research and medical diagnostics. Detection of a target sequence can be used to identify and/or type a specific DNA or RNA molecule and to uncover mutations.

Numerous methods and techniques exist in the art with which detection and/or identification of a target sequence can be effected. For example, polynucleotide sequencing methods can be used to determine the nucleotide sequence of a target DNA or RNA molecule. The methods typically used for sequencing include the Sanger dideoxy method, see, e.g., Sanger et al. (1977) Proc. Natl. Acad. Sci. USA, 74:5463–5467, or the Maxam and Gilbert method, see, e.g., Maxam et al, (1980) Methods in Enzymology, 65:499–559.

The polymerase chain reaction (PCR) can also be used to detect the presence of a target sequence in a sample. PCR utilizes oligonucleotide primers which specifically bind regions within the target sequence to amplify the target nucleic acid sequence, the generation of amplification products is indicative of the presence of the target sequence.

Another approach to target nucleic acid identification involves hybridizing an oligonucleotide probe to the target nucleic acid sequence wherein hybridization is indicative of the presence thereof.

An oligonucleotide probe binds to a target nucleic acid by forming hydrogen bonds between bases in the target and the oligonucleotide. Common B-DNA has conventional adenine-thymine (A-T) and guanine-cytosine (G-C) Watson and Crick base pairs with two and three hydrogen bonds formed therebetween, respectively. Conventional hybridization technology is based upon the capability of sequence-specific DNA or RNA oligonucleotide probes to bind to a complementary target nucleic acid via Watson-Crick hydrogen bonds. However, other types of internucleotide hydrogen bonding patterns are known wherein atoms not involved in Watson-Crick base pairing to a first nucleotide can form hydrogen bonds to another nucleotide. For example, thymine (T) can bind to an AT Watson-Crick base pair via hydrogen bonds to the adenine, thereby forming a T-AT base triad. Hoogsteen (1959, Acta Crystallographica 12:822) first described the alternate hydrogen bonds present in T-AT and C-GC base triads. More recently, G-TA base triads, wherein guanine can hydrogen bond with a central thymine, have been observed (Griffin et al., 1989, Science 245:967–971).

Oligonucleotide probes which can bind to a target nucleic acid with both Watson-Crick and non-Watson-Crick hydrogen bonds form extremely stable complexes with the target nucleic acid and as such have a variety of research and diagnostic utilities.

For example, oligonucleotides can be used as probes for target nucleic acids that are immobilized onto a filter or membrane, or are present in tissues, e.g. as described in Sambrook et al., (1989, Molecular Cloning: A Laboratory Manual, Vols. 1–3, Cold Spring Harbor Press, NY). However, the utility of linear oligonucleotide probes is frequently limited by their poor binding stability and selectivity.

Another example includes solution phase detection methods. Several solution-phase detection methods, sometimes referred to as homogeneous assays, are known. The term "homogeneous" is used in the art to refer to methods performed without separating unhybridized oligonucleotide probes from probe-target hybrids. These methods often rely upon the fact that the fluorescence of many fluorescent labels can be affected by the conformation of the oligonucleotide probe or by the immediate chemical environment.

U.S. Pat. No. 5,876,930 to Livak et al. discloses a method for identifying a target nucleic acid sequence. The method utilizes an oligonucleotide probe which includes a fluorescent reporter molecule and a quencher molecule capable of quenching the fluorescence of the reporter molecule. The oligonucleotide probe according to this method is constructed such that the probe exists in at least one single-stranded conformation when unhybridized, where the quencher molecule is near enough to the reporter molecule to quench the fluorescence of the reporter molecule. The oligonucleotide probe also exists in at least one conformation when hybridized to a target nucleic acid where the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, this method enables to determine the presence of a specific target nucleic acid sequence based on a change in the fluorescence intensity of the reporter molecule, the quencher molecule, or a combination thereof. The limitation of this approach is that no signal amplification is enabled, resulting in inability of detecting low target concentrations. In addition, this method is inherently characterized by a high background signal.

U.S. Pat. No. 5,925,517 to Tyagi et al. discloses unimolecular and bimolecular hybridization probes for the detection of nucleic acid target sequences. The probes include a target complement sequence, an affinity pair holding the probe in a closed conformation in the absence of target sequence, and either a label pair that interacts when the probe is in the closed conformation or, for certain unimolecular probes, a non-interactive label. Hybridization of the target and target complement sequences shifts the probe to an open conformation. The shift is detectable due to reduced interaction of the label pair or by decreasing a signal from a non-inverted label. Certain unimolecular probes can discriminate between target and non-target sequences differing by as little as one nucleotide. The limitation of this approach is that no signal amplification is enabled, resulting in inability of detecting low target concentrations. In addition, this method is inherently characterized by a high background signal.

U.S. Pat. No. 5,866,336 to Nazarenko et al. describes labeled nucleic acid amplification oligonucleotides, which can be linear or hairpin primers or blocking oligonucleotides. The oligonucleotides disclosed by Nazarenko are labeled with donor and/or acceptor moieties of molecular energy transfer pairs. The moieties can be fluorophores, such that fluorescent energy emitted by the donor is absorbed by the acceptor. The acceptor may be a fluorophore that fluoresces at a wavelength different from the donor moiety, or it may be a quencher. These oligonucleotides are configured so that a donor moiety and an acceptor moiety are incorporated into the amplification product. The invention also provides methods and kits for directly detecting amplification products employing the nucleic acid amplification primers. When labeled linear primers are used, treatment with exonuclease or by using specific temperature eliminates the need for separation of unincorporated primers. This "closed-tube" format greatly reduces the possibility of carryover contamination with amplification products, provides for high throughput of samples, and may be totally automated.

U.S. Pat. No. 4,766,062 to Diamond et al. describes a diagnostic reagent containing a complex of a probe polynucleotide bound via purine/pyrimidine hydrogen bonding to a labeled polynucleotide. The probe contains a target binding region capable of binding to a target sequence of a biological sample. U.S. Pat. No. 4,766,062 further describes a method in which contact with a sample containing the target nucleotide sequence causes binding, initially between the target and a single-stranded portion of the target binding region. Thereafter the labeled polynucleotide is displaced from the complex of branch migration of into the binding region. Determination of displaced labeled polynucleotide gives a value which is a function of the presence and concentration of target nucleotide sequence in the sample.

U.S. Pat. No. 5,451,503 to Hogan et al., which is discussed in more detail in the preferred embodiments section that follows, teaches of nucleic acid hybridization probes having at least one nucleic acid strand which has at least two separate target specific regions that hybridize to a target nucleic acid sequence, and at least two distinct arm regions that do not hybridize with the target nucleic acid but possess complementary regions that are capable of hybridizing with one another. These regions are designed such that, under appropriate hybridization conditions, the complementary arm regions will not hybridize to one another in the absence of the target nucleic acid; but, in the presence of target nucleic acid the target-specific regions of the probe will anneal to the target nucleic acid, and the complementary arm regions will anneal to one another, thereby forming a branched nucleic acid structure which is useful for target nucleic acid sequence detection.

Although the above mentioned methods are less complicated to perform than simple oligonucleotide probe detection methods such as that described by Sambrook et al. in which oligonucleotide probes are used to target nucleic acids that are immobilized onto a filter or membrane, some limitations still apply. For example, a method which is simple to perform such as that described by Livak et al. can yield false positive results since hybridization to non-target sequences will also yield, in some cases, a positive result.

In general, the above methods are characterized by low signal and high background. Hogan et al. teaches signal amplification by template recycling and background reduction by appropriate selection of the length of the arm regions of the oligonucleotides employed thereby. Methods which are aimed at producing more accurate results are oftentimes more complicated to perform. However, as is further shown and exemplified hereinunder, improved methods for signal amplification an background reduction are still required.

Thus, the present invention discloses novel oligonucleotides utilizable in a homogeneous detection method of target nucleic acid sequences, which method depends on the generation of a specific cleavage site in a hybridized, conformationaly changed oligonucleotide, and as such the present invention provides a simple method of target nucleic acid detection while retaining a high level of specificity.

SUMMARY OF THE INVENTION

According to one aspect of the present invention there is provided an oligonucleotide or assembly of oligonucleotides useful in detecting a presence or an absence of a target nucleic acid sequence in a sample, the oligonucleotide or assembly of oligonucleotides comprising (a) a first region and a second region, at least a portion of the first region and at least a portion of the second region each being capable of hybridizing under predetermined hybridization conditions with the target nucleic acid sequence; and (b) a third region and a fourth region, the third region and the fourth region being linked to the first region and the second region, respectively, a first portion and a second portion of the oligonucleotide or assembly of oligonucleotides being capable of forming a first duplex structure therebetween under the predetermined hybridization conditions; the first, second, third and fourth regions of the oligonucleotide or assembly of oligonucleotides being selected such that upon hybridization under the predetermined hybridization conditions of the first region and the second region with the target nucleic acid sequence, the first duplex structure dissociates and a portion of the third region and a portion of the fourth region form a second duplex structure therebetween, the second duplex structure including a nucleic acid cleaving agent recognition sequence which is absent from the first duplex structure and which, when cleaved, indicates hybridization of the oligonucleotide or assembly of oligonucleotides to the target nucleic acid sequence and therefore indicates the presence of the target nucleic acid in the sample.

According to another aspect of the present invention there is provided a method of detecting a presence or an absence of a target nucleic acid sequence in a sample, the method comprising the steps of (a) contacting the sample with an oligonucleotide or assembly of oligonucleotides under predetermined hybridization conditions so as to form a reaction mixture, the oligonucleotide or assembly of oligonucleotides including (i) a first region and a second region, at least a portion of the first region and at least a portion of the second region each being capable of hybridizing with the target nucleic acid sequence; and (ii) a third region and a fourth region, the third region and the fourth region being linked to the first region and the second region, respectively, a first portion and a second portion of the oligonucleotide or assembly of oligonucleotides being capable of forming a first duplex structure therebetween under the predetermined hybridization conditions; the first, second, third and fourth regions of the oligonucleotide or assembly of oligonucleotides being selected such that upon hybridization under the predetermined hybridization conditions of the first region and the second region with the target nucleic acid sequence, the first duplex structure dissociates and a second portion of the third region and a second portion of the fourth region form a second duplex structure therebetween, the second duplex structure including a nucleic acid cleaving agent recognition sequence which is absent from the first duplex structure; (b) adding a nucleic acid cleaving agent to the reaction mixture, such that, if the target nucleic aid sequence is present in the sample, the nucleic acid cleaving agent recognition sequence is formed and cleaved by the cleaving agent; and (c) monitoring cleavage of the nucleic acid cleaving agent recognition sequence by the nucleic acid cleaving agent; wherein cleavage of the nucleic acid cleaving agent recognition sequence by the nucleic acid cleaving agent indicates hybridization of the oligonucleotide or assembly of oligonucleotides to the target nucleic acid sequence and therefore the presence of the target nucleic acid in the sample.

According to further features in preferred embodiments of the invention described below, the first portion and the second portion of the oligonucleotide or assembly of oligonucleotides being capable of forming the the duplex structure therebetween under the predetermined hybridization conditions are derived from the third and fourth regions, respectively.

According to still further features in the described preferred embodiments the first, second, third and fourth regions of the oligonucleotide or assembly of oligonucleotides are further selected such that following cleavage of the nucleic acid cleaving agent recognition sequence, the first and second regions dissociate from the target nucleic acid sequence, thereby enabling recycling of the target nucleic acid sequence.

According to still another aspect of the present invention there is provided an oligonucleotide system useful for detecting a presence or an absence of a target nucleic acid sequence in a sample comprising at least a first oligonucleotide and a second oligonucleotide, each of the first oligonucleotide and the second oligonucleotide including a first region being capable of hybridizing with the target nucleic acid sequence under predetermined hybridization conditions, each of the first oligonucleotide and the second oligonucleotide further including a second region, wherein upon hybridization, at least a portion of the second regions of the first oligonucleotide and the second oligonucleotide form a duplex structure including a nucleic acid cleaving agent recognition sequence, the second regions of the first oligonucleotide and the second oligonucleotide being selected such that in a presence of a nucleic acid cleaving agent recognizing the nucleic acid cleaving agent recognition sequence, only the first oligonucleotide is cleavable by the nucleic acid cleaving agent.

According to an additional aspect of the present invention there is provided a method of detecting a presence or an absence of a target nucleic acid sequence in a sample, the method comprising the steps of (a) contacting the sample with an oligonucleotide system under hybridization conditions so as to form a reaction mixture, the oligonucleotide system including at least a first oligonucleotide and a second oligonucleotide, each of the first oligonucleotide and the second oligonucleotide including a first region being capable of hybridizing under predetermined hybridization conditions with the target nucleic acid sequence, each of the first oligonucleotide and the second oligonucleotide further including a second region, wherein upon hybridization under the predetermined hybridization conditions, at least a portion of the second regions of the first oligonucleotide and the second oligonucleotide form a duplex structure including a nucleic acid cleaving agent recognition sequence, the second regions of the first oligonucleotide and the second oligonucleotides being selected such that in a presence of a nucleic acid cleaving agent recognizing the nucleic acid cleaving agent recognition sequence, only the first oligonucleotide is cleavable by the nucleic acid cleaving agent; (b) adding the nucleic acid cleaving agent to the reaction mixture, such that, if the target nucleic acid sequence is present in the sample, the nucleic acid cleaving agent recognition sequence is cleaved by the nucleic acid cleaving agent; and (c) monitoring cleavage of the nucleic acid cleaving agent recognition sequence by the nucleic acid cleaving agent; wherein cleavage of the nucleic acid cleaving agent recognition sequence by the nucleic acid cleaving agent indicates hybridization of the oligonucleotide system to the target nucleic acid sequence and therefore the presence of the target nucleic acid in the sample.

According to further features in preferred embodiments of the invention described below, the first and second regions of the first and second oligonucleotides are selected such that upon cleavage of the first oligonucleotide, the first region of the first oligonucleotide dissociates from the target nucleic acid sequence.

According to still further features in the described preferred embodiments the first region of the second oligonucleotide is selected such that under the predetermined hybridization conditions and following dissociation of the first oligonucleotide, the first region of the second oligonucleotide remains hybridized to the target nucleic acid sequence, thereby allowing recycling of the target nucleic acid sequence with respect to the first oligonucleotide.

According to yet an additional aspect of the present invention there is provided an oligonucleotide system useful for detecting a presence or an absence of a target nucleic acid sequence in a sample comprising at least a first oligonucleotide and a second oligonucleotide, each of the first oligonucleotide and the second oligonucleotide including a first region being complementary or substantially complementary to the target nucleic acid sequence, each of the first oligonucleotide and the second oligonucleotide further including a second region, the second regions of the first and second oligonucleotides being complementary or substantially complementary and being selected such that upon annealing therebetween the second regions form a duplex structure including a nucleic acid cleaving agent recognition sequence, wherein under predetermined hybridization conditions the first region of the first oligonucleotide is stably hybridizable with the target nucleic acid sequence only if the first region of the second oligonucleotide is stably hybridizable with the nucleic acid target sequence.

According to still an additional aspect of the present invention there is provided a method of detecting a presence or an absence of a target nucleic acid sequence in a sample, the method comprising the steps of (a) contacting the sample with an oligonucleotide system so as to form a reaction mixture, the oligonucleotide system including at least a first oligonucleotide and a second oligonucleotide, each of the first oligonucleotide and the second oligonucleotide including a first region being complementary or substantially complementary to the target nucleic acid sequence, each of the first oligonucleotide and the second oligonucleotide further including a second region, the second regions of the first and second oligonucleotides being complementary or substantially complementary and being selected such that upon annealing therebetween the second regions form a duplex structure including a nucleic acid cleaving agent recognition sequence, wherein under the predetermined hybridization conditions the first region of the first oligonucleotide is stably hybridizable with the target nucleic acid sequence only if the first region of the second oligonucleotide is stably hybridizable with the nucleic acid target sequence; (b) adding a nucleic acid cleaving agent to the reaction mixture, such that, if the target nucleic acid sequence is present in the sample, the nucleic acid cleaving agent recognition sequence is cleaved by the nucleic acid cleaving agent; and (c) monitoring cleavage of the nucleic acid cleaving agent recognition sequence by the nucleic acid cleaving agent; wherein cleavage of the nucleic acid cleaving agent recognition sequence by the nucleic acid cleaving agent indicates hybridization of the oligonucleotide system to the target nucleic acid sequence and therefore the presence of the target nucleic acid in the sample.

According to further features in preferred embodiments of the invention described below, under the predetermined hybridization conditions the second regions of the first and second oligonucleotides are substantially non-hybridizable with one another per se.

According to still further features in the described preferred embodiments the second regions of the first oligonucleotide and the second oligonucleotide are selected such that in a presence of a nucleic acid cleaving agent recognizing the nucleic acid cleaving agent recognition sequence, only the first oligonucleotide is cleavable by the nucleic acid cleaving agent.

According to still further features in the described preferred embodiments the first and second regions of the first and second oligonucleotides are selected such that under the predetermined hybridization conditions and upon cleavage of the first oligonucleotide, the first region of the first oligonucleotide dissociates from the target nucleic acid sequence.

According to still further features in the described preferred embodiments at least one nucleotide or internucleotidic bond of the second oligonucleotide which forms a part of the nucleic acid cleaving agent recognition sequence is a modified or analogous nucleotide or internucleotidic bond, selected so as to prevent cleavage of the second oligonucleotide by the nucleic acid cleaving agent.

According to still further features in the described preferred embodiments the duplex structure is formed in part by self annealing of a portion of the second region of the first oligonucleotide.

According to still further features in the described preferred embodiments the second regions of the first and second oligonucleotides are selected such that the nucleic acid cleaving agent recognition sequence is characterized by a nick replacing an internucleotidic bond cleavable by the nucleic acid cleaving agent.

According to yet a further aspect of the present invention there is provided an oligonucleotide system useful for detecting a presence or an absence of a target nucleic acid sequence in a sample comprising at least a first oligonucleotide and a second oligonucleotide, each of the first oligonucleotide and the second oligonucleotide including a first region being complementary or substantially complementary to the target nucleic acid sequence, each of the first oligonucleotide and the second oligonucleotide further including a second region, the second regions of the first and second oligonucleotides being complementary or substantially complementary and being selected such that upon annealing therebetween the second regions form a duplex structure including a nucleic acid cleaving agent recognition sequence, wherein under predetermined hybridization conditions the first regions of the first oligonucleotide and the second oligonucleotide are stably hybridizable with the target nucleic acid sequence, and the second regions of the first oligonucleotide and the second oligonucleotide are stably hybridizable therebetween only when the first oligonucleotide, the second oligonucleotide and the target nucleic acid sequence are co-annealed.

According to still a further aspect of the present invention there is provided a method of detecting a presence or an absence of a target nucleic acid sequence in a sample, the method comprising the steps of (a) contacting the sample with an oligonucleotide system so as to form a reaction mixture, the oligonucleotide system including at least a first oligonucleotide and a second oligonucleotide, each of the first oligonucleotide and the second oligonucleotide including a first region being complementary or substantially complementary to the target nucleic acid sequence, each of the first oligonucleotide and the second oligonucleotide further including a second region, the second regions of the first and second oligonucleotides being complementary or substantially complementary and being selected such that upon annealing therebetween the second regions form a duplex structure including a nucleic acid cleaving agent recognition sequence, wherein under predetermined hybridization conditions the first regions of the first oligonucleotide and the second oligonucleotide are stably hybridizable with the target nucleic acid sequence, and the second regions of the first oligonucleotide and the second oligonucleotide are stably hybridizable therebetween only when the first oligonucleotide, the second oligonucleotide and the target nucleic acid sequence are co-annealed; (b) adding a nucleic acid cleaving agent to the reaction mixture, such that, if the target nucleic acid sequence is present in the sample, the nucleic acid cleaving agent recognition sequence is cleaved by the nucleic acid cleaving agent; and (c) monitoring cleavage of the nucleic acid cleaving agent recognition sequence by the nucleic acid cleaving agent; wherein cleavage of the nucleic acid cleaving agent recognition sequence by the nucleic acid cleaving agent indicates hybridization of the oligonucleotide system to the target nucleic acid sequence and therefore the presence of the target nucleic acid in the sample.

The present invention successfully addresses the shortcomings of the presently known configurations by providing oligonucleotides or assemblies of oligonucleotides which enable the simple and efficient detection of target nucleic acid sequences while reducing the reaction order or the background signal generation.

BRIEF DESCRIPTION OF THE DRAWINGS

The file of this patent contains at least one drawings executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic depiction demonstrating the steps of a detection method according to one preferred aspect of the present invention.

FIG. 2 depicts the structure of a single oligonucleotide and a nucleotide assembly of the present invention when hybridized to a target nucleic acid sequence.

Figure 3A:
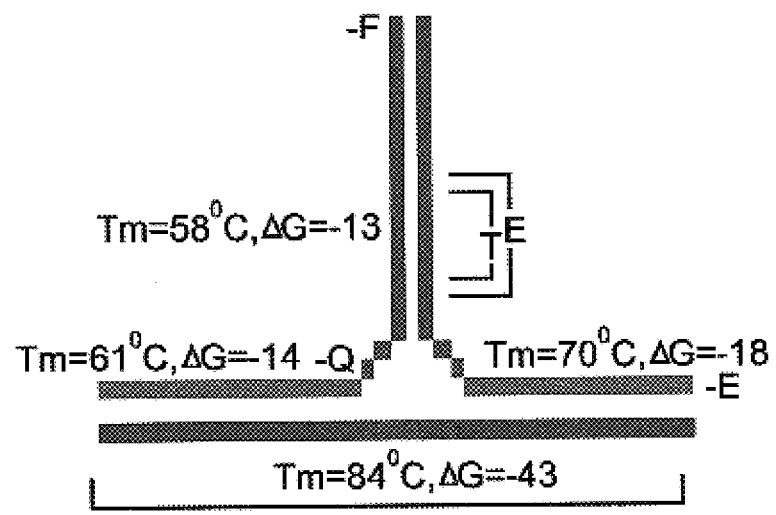
Figure 3B:
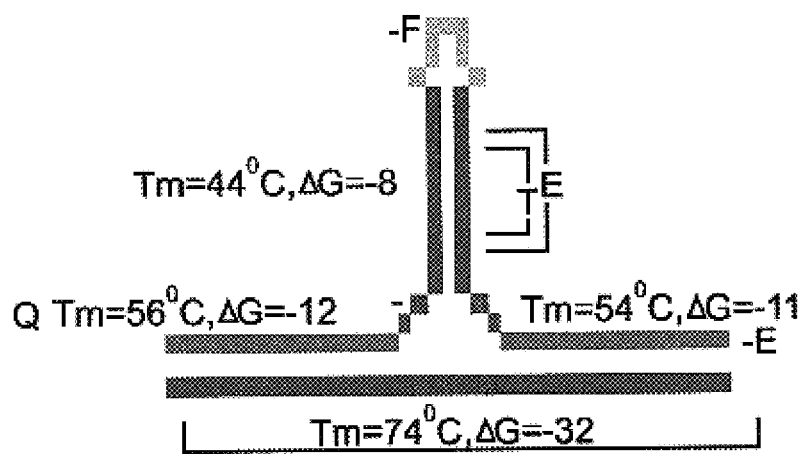

FIGS. 3a–b depict the domain structure and regions of a paired oligonucleotide (FIG. 3a) and a looped oligonucleotide (FIG. 3b) according to the present invention showing the melting temperature (Tm) and free energy (ΔG) of the target hybridizing (first and second regions) and stem forming regions (third and fourth regions).

Figure 4:
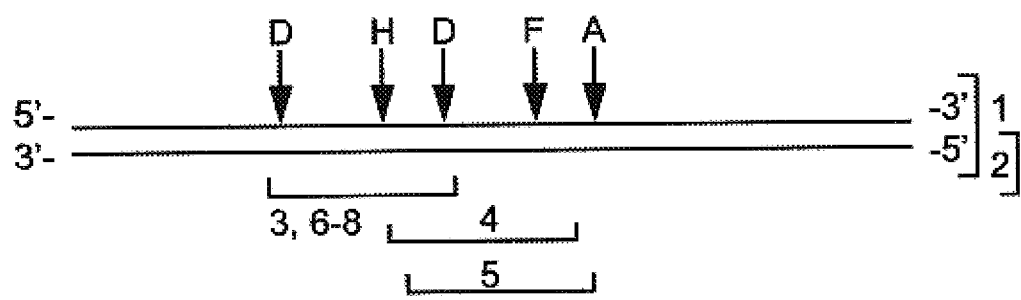

FIG. 4 is a restriction map showing the regions of the various CMV-DNA preparations (1–8) derived from a 263 bp CMV-DNA template fragment and which were used as target nucleic acid sequences while reducing the present invention to practice. Arrows indicate the site of enzymatic cleavage. A=AflII; D–DdeI; F=Fnu4HI; H=HaeIII.

FIGS. 5a–e are photographs of 12.5% native polyacrylamide gels depicting the effects of stem and arms regions on hybridization of paired biotinylated oligonucleotide probes to CMV-DNA. The biotinylated oligonucleotides were visualized as described in the Examples section that follows. The number at the bottom of each lane represents the hybridization incubation temperature. Asterisk—biotin tag.

Figure 6:
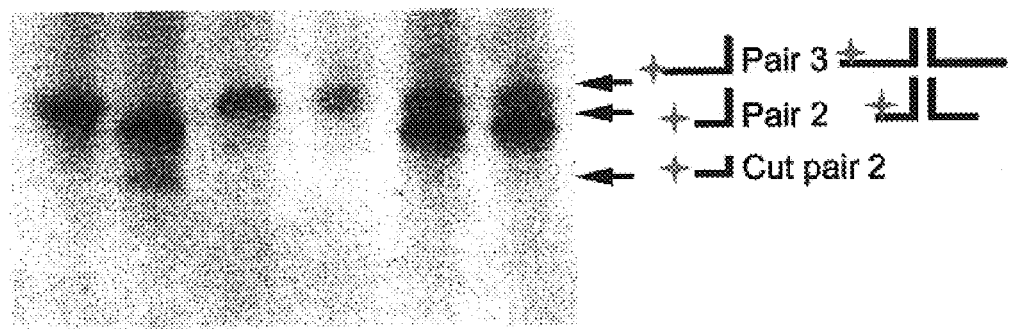

FIG. 6 is a photograph of a 12.5% native polyacryalide gel depicting the effect of arm region length on recycling of CMV-DNA by paired oligonucleotide probes. Pair 2 and pair 3 were incubated in the presence (+) or absence (−) of template DNA. Following the hybridization step, 0.17 unit/µl of BstBI was added to each tube and cleavage was allowed to proceed for 2 h. Biotinylated fragments were visualized as described in the Examples section that follows. Asterisk—biotin tag.

Figure 7:
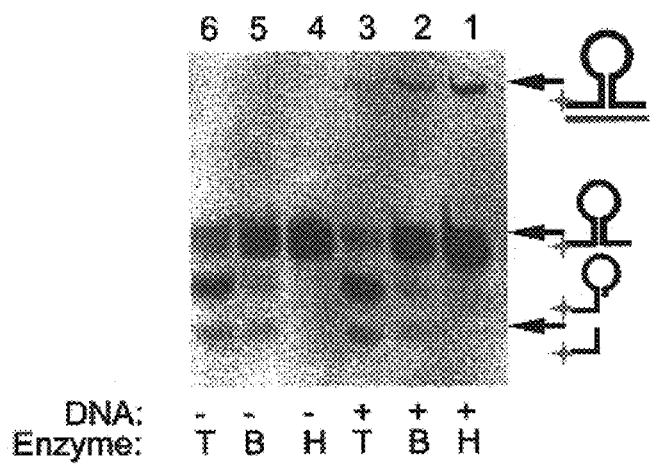

FIG. 7 is a photograph of a 12.5% native polyacrylamide gel depicting chromatographic separation of a single looped oligonucleotide probe, either prehybridized with template DNA (+) or not (−) and either cleaved by TaqI(T) and BstBI (B) or not (H). Asterisk—biotin tag.

Figures 8A, 8B:
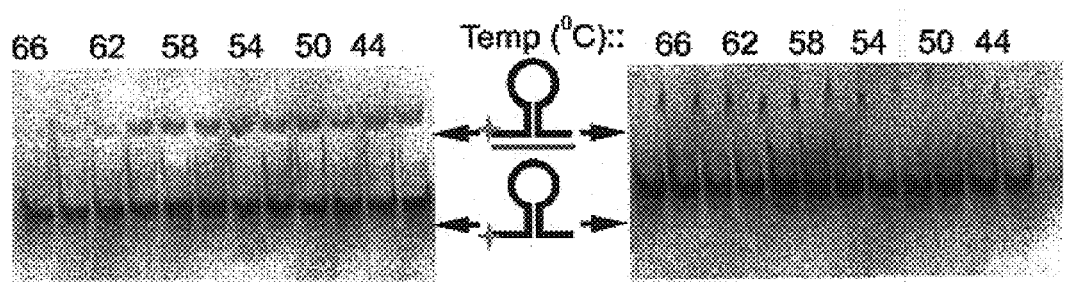

FIGS. 8a–b are photographs on 12.5% native polyacrylamide gels depicting chromatographic separation of a hybridized and non-hybridized looped biotinylated oligonucleotide reacted with a long double stranded target DNA (p.CMV-263.ds, Table 1) (FIG. 8a) or a shorter double stranded target DNA (p.DMV-2.st, Table 1) (FIG. 8b). The biotinylated oligonucleotide was visualized as described in the Examples section that follows. The number at the top of each lane represents the hybridization incubation temperature. Asterisk—biotin tag.

Figures 9A, 9B:
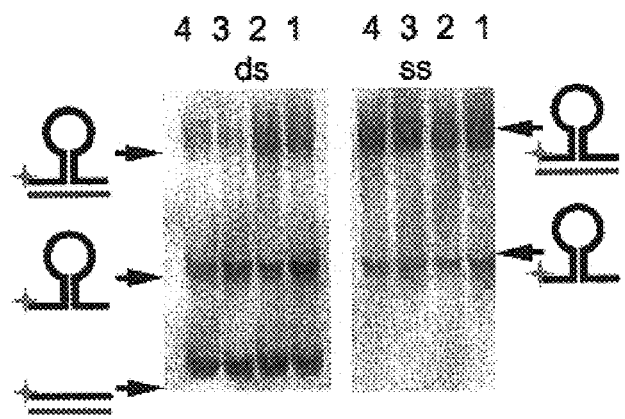

FIGS. 9a–b are photographs of 12.5% native polyacrylamide gels depicting chromatographic separation of looped biotinylated oligonucleotides reacted with either single stranded target DNA (antisense CMV-2.st, Table 1) or with ds target DNA of the same length (sny.DMV-2.st, Table 1). The biotinylated oligonucleotide and hybridization products were visualized as described in the Examples section that follows. Asterisk—biotin tag.

FIGS. 10a–c are photographs of 12.5% polyacrylamide gels depicting chromatographic separation of a looped oligonucleotide probe following hybridization with decreasing concentrations of single stranded target DNA and following enzymatic cleavage. The assay consisted of two identical sets of seven tubes, each supplemented with decreasing amounts of single stranded CMV target DNA (35 nucleotide long) (antisense CMV-2.st, Table 1). The molar ratio between antisense CMV-2.st and the looped oligonucleotide probes was 1:1, 1:4, 1:10, 1:40, 1:100, 1:400 in tubes 1 to 6, respectively. No CMV-DNA was added to tube number 7. FIG. 10a represents samples at the end of a hybridization step. FIG. 10b represents samples following cleavage of the oligonucleotide for two hours and separation under denaturing conditions to detect single stranded biotinylated fragments. FIG. 10c represents samples identical to that of FIG. 10b but separated on a native gel, to detect both double stranded and single stranded fragments. Biotinylated fragments were visualized as described in the Examples section that follows. Asterisk—biotin tag.

Figure 11A:
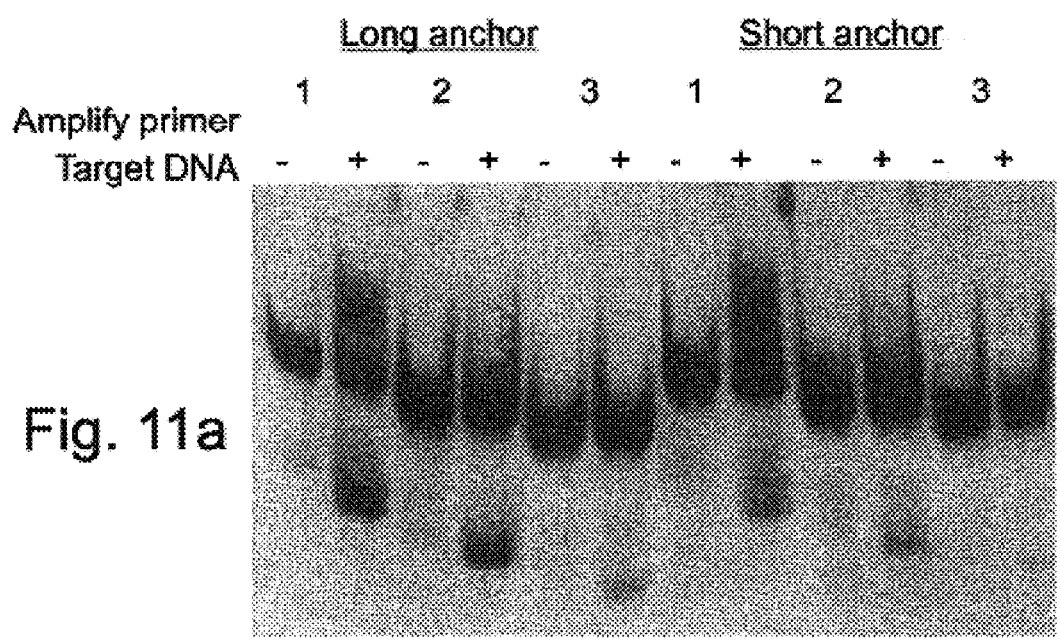
Figure 11B:
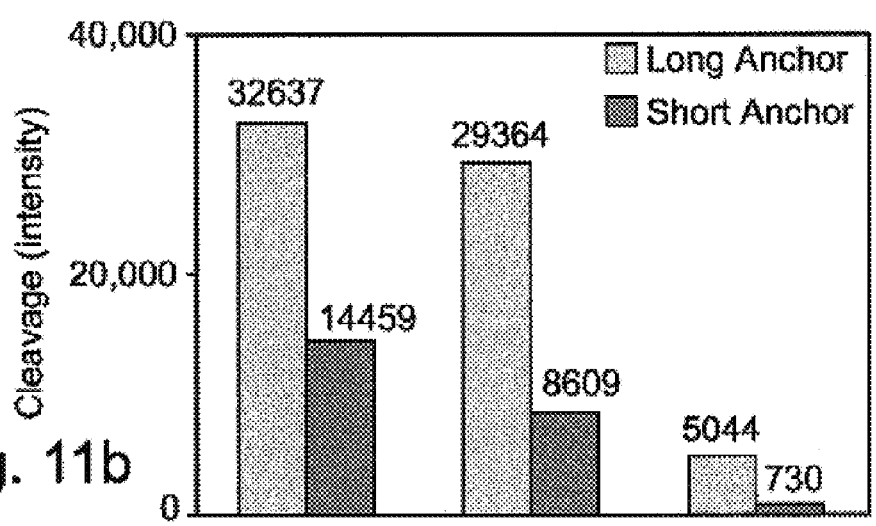
Figure 11C:
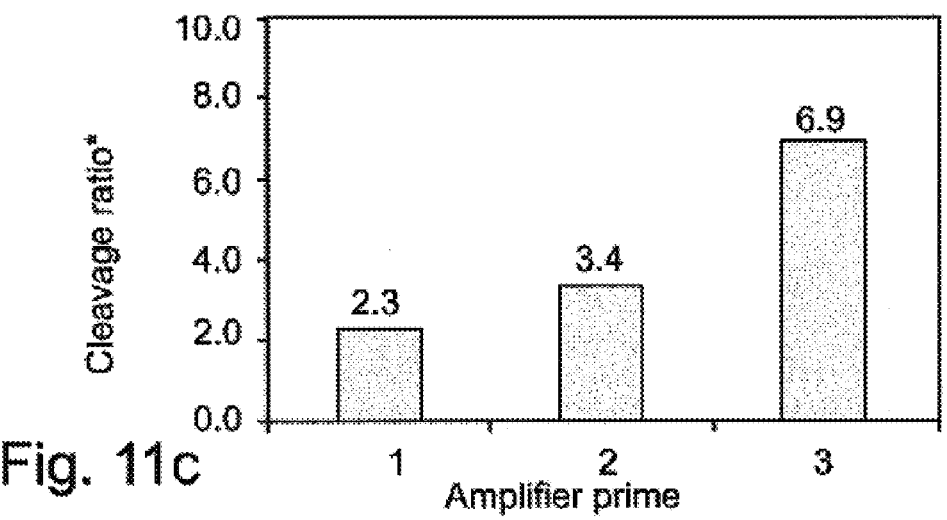

FIGS. 11a–c illustrate the effect of long and short oligonucleotide anchors on cleaved-product accumulation. A 12.5% polyacrylamide gel electrophoresis of target and probe members following cleavage was blotted onto a membrane (FIG. 11a) which was scanned and analyzed. FIGS. 11b–c illustrate the cleavage efficiency (FIG. 11b) and the increase in cleavage of the amplifier oligonucleotide member (FIG. 11c) when longer anchor members are utilized.

Figure 12:
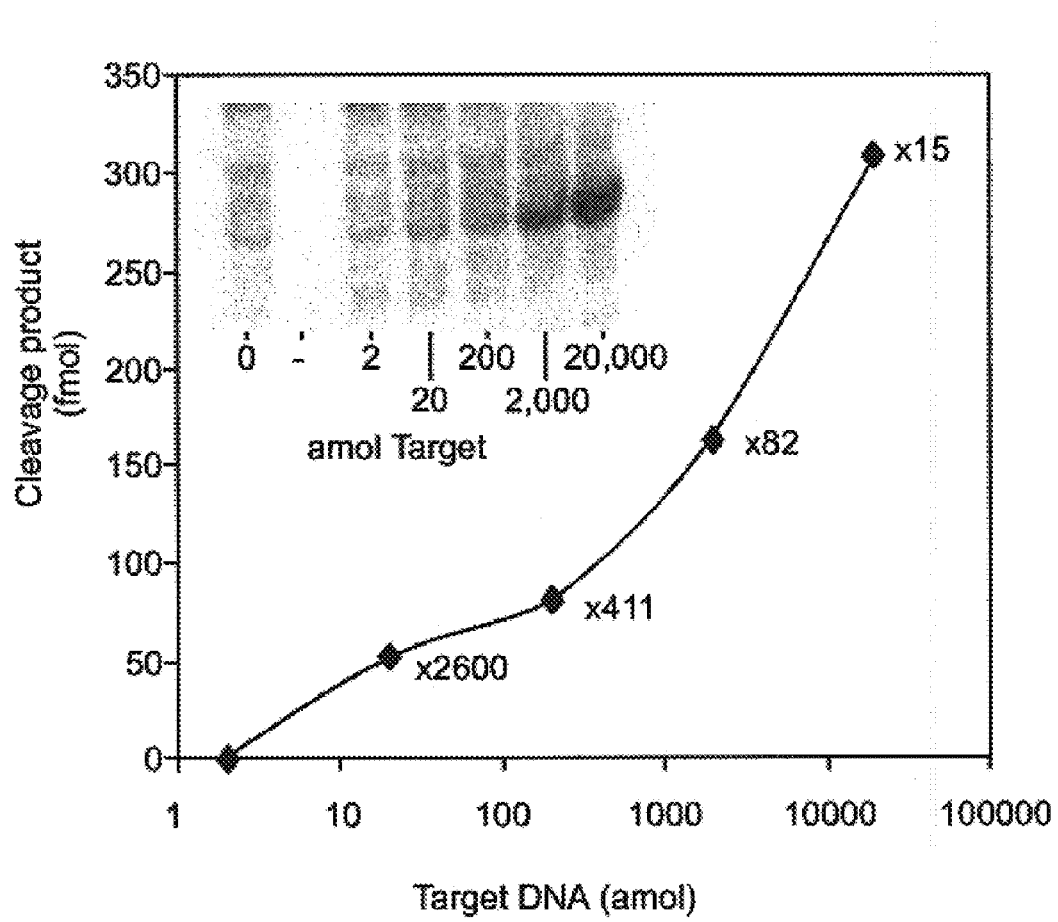

FIG. 12 is a graph illustrating amplifier cleavage product as a function of target DNA concentration; amplification factors are presented to the right of each data point. The Inset illustrates a 15% denaturing polyacrylamide gel separation of samples containing 0, 2 amol, 20 amol, 200 amol, 2 fmol and 20 fmol of the target.

DESCRIPTION OF THE PREFERRED EMBODIMENTS

The present invention is of oligonucleotides and method employing same which can be used for the detection of target nucleic acid sequences. Specifically, the present invention can be used to detect the presence or absence of a specific target nucleic acid sequence by utilizing oligonucleotide probes which when annealed to the template sequence (s) form an intrinsic (endogenous) cleavage site therebetween. Subsequent cleavage of this cleavage site leads to the generation of a detectable signal and may also dissociate one or more of the oligonucleotide(s) from the target nucleic acid sequence, and as such allows template recycling and signal amplification.

The principles and operation of the oligonucleotides and methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As used herein the terms "oligonucleotide" and "probe" and the phrase "oligonucleotide probe" are used interchangeably to refer to a single stranded nucleic acid molecule or assembly of single stranded nucleic acid molecules which can exhibit one or more partial double stranded conformations. Such molecule(s) can be used according to the present invention for the detection of the presence or absence of a single stranded or a double stranded (following appropriate denaturation) target nucleic acid sequence as is further described herein.

As used throughout, the term "template" or the phrase "target nucleic acid sequence" refer to a nucleic acid template which is either naturally in a single stranded form, such as messenger RNA, or is denatured into a single stranded form, such as DNA. The target nucleic acid sequence according to the present invention can be in a crude, partially purified or purified form and may have varying degree of complexity depending on its origin. As used herein a specific target nucleic acid sequence may differ from another specific target nucleic acid sequence by even a single nucleotide, e.g., a point mutation, or by a plurality of nucleotides.

As herein the phrase "complementary or substantially complementary" refers to sequences that may base pair under predetermined hybridization conditions of temperature and ionic strength and/or the presence of template. "Substantially complementary" refers to at least 50% complementary, preferably, at least 60% complementary, more preferably, at least 70% complementary, still preferably, at least 80% complementary, advantageously, between 90% and 100% complementary.

As is further detailed hereinunder, to enable detection, the oligonucleotide or oligonucleotides assembly of the present invention are preferably tagged with a detection moiety or moieties. It will be appreciated however, and it is further detailed hereinbelow, that detection according to the present invention can also be effected without the incorporation of such detection moieties onto these oligonucleotide(s).

The following paragraphs describe oligonucleotide probes which are taught by the prior art yet are used in accordance with the teachings of the present invention with certain restrictions to be further emphasized below, which restrictions result in far superior detection of target nucleic acids due to signal amplification and/or reduction of background signal.

Thus, according to one aspect of the present invention there is provided an oligonucleotide or an assembly of the oligonucleotides useful for detecting the presence or absence of a target nucleic acid sequence in a sample. The oligonucleotide or the assembly of oligonucleotides according to this aspect of the present invention is capable of forming a duplex structure intrinsic to the oligonucleotide or the assembly of oligonucleotides upon hybridization with the target nucleic acid sequence, meaning that the duplex structure formed as a result of template hybridization includes only sequences contributed by the oligonucleotide or the assembly of oligonucleotides.

The duplex structure thus formed includes a nucleic acid cleaving agent recognition sequence (site), such that subsequent cleavage of this site is detectable, e.g., via the production of a detectable signal. The specifics of a detection reaction including preferred conditions and solutions and preferred target nucleic acid sequence-oligonucleotide(s) ratios, and the like, are further described throughout the Examples section that follows in context of a variety of particular oligonucleotide(s) which correspond to the above criteria.

A typical configuration of the oligonucleotide or the assembly of oligonucleotides of the present invention, includes a first region and a second region. At least a portion of the first region and at least a portion of the second region are each independently complementary to at least a portion of the target nucleic acid sequence. That is to say that portions of the target nucleic acid sequence can co-hybridize to at least a portion of the first region and at least a portion of the second region at the same time. Thus, at least a portion of the first region and at least a portion of the second region hybridize to different, typically adjacent, subregions of the target nucleic acid sequence.

The oligonucleotide or the assembly of oligonucleotides of this aspect of the present invention further include a third region and a fourth region which are respectively linked either directly or through a spacer region of say 1–6 nucleotide bases to the first region and the second region, preferably through a covalent phosphodiester bond or an analog thereof.

The third and fourth regions are configured such that upon hybridization of the first region and the second region with the target nucleic acid sequence, at least a portion of the third region and at least a portion of the fourth region anneal to form a duplex structure therebetween. This duplex structure includes a nucleic acid cleaving agent recognition sequence which is described in more detail hereinbelow and in the Examples section that follows.

Cleavage of the recognition sequence by an appropriate nucleic acid cleaving agent leads to the separation of at least a portion of at least one of the third and the fourth regions from the first and the second regions, respectively.

As is further detailed hereinbelow, this cleavage and separation, which occurs according to the present invention substantially only or preferably in cases in which the oligonucleotide or the assembly of oligonucleotides hybridize with the target nucleic acid sequence, is used to detect the presence of that specific target nucleic acid sequence.

It will be appreciated that since the first and second regions of the oligonucleotide or assembly of oligonucleotides is responsible for hybridizing to a specific template nucleic acid sequence, these regions are synthesized accordingly to recognize and anneal to the target nucleic acid sequence. As such, when synthesizing probes according to the teachings of the present invention, the first and second regions must be designed in accordance with the specific target nucleic acid sequence targeted to be detected. On the other hand, since the third and fourth regions are responsible for forming the intrinsic duplex and the cleaving agent recognition sequence, these regions are typically universal and as such can be utilized by many specific oligonucleotides of the present invention. However, there are cases in which the "universal" third and fourth regions can not be used with a target specific first and second regions. For example, when such use it not energetically favorable or when the cleaving agent recognition sequence included within the duplex is also present in the first and/or the second regions when hybridized to the target. Under such circumstances, the third and fourth regions must be suitably redesigned.

According to one embodiment of the present invention the assembly of oligonucleotides is a bi-molecular oligonucleotide including two oligonucleotide molecules, such that a first oligonucleotide of the assembly includes the above mentioned first and third regions and further such that a second oligonucleotide of the assembly includes the above mentioned second and fourth regions.

According to another embodiment of the present invention a single oligonucleotide molecule is employed. In this case, the third and fourth regions are linked therebetween, preferably via a covalent phosphodiester bond, such that a stem and loop structure is formed by the third and fourth regions when at least a portion of the third region and at least a portion of the fourth region anneal to form the duplex described above.

According to another embodiment of the present invention, both the first and second regions of the oligonucleotide dissociate from the target nucleic acid sequence upon separation of at least a portion of the third and fourth regions from the first region and the second region. In this case, cleavage and subsequent separation of either the third or fourth regions, or both, leads to the dissociation of the first and/or second regions from the target nucleic acid sequence. This dissociation allows a second identical oligonucleotide molecule to hybridize to the target nucleic acid sequence and go through a similar process of cleavage and separation.

It will be appreciated that in the case of a bimolecular probe in which the third and fourth regions are not attached therebetween, separation thereof from the first and second regions, respectively, following cleavage is not interdependent.

As so far described, the above oligonucleotide probes which are further described and their use exemplified in Example 3 under "Paired probes-First generation" and in Example 6 under "Single probes-First generation" are similar in structure and function to the oligonucleotide probes described by Hogan et al., (U.S. Pat. No. 5,451,503).

Although these oligonucleotide probe configurations can be utilized for detection of target nucleic acid sequences they still suffer from several inherent limitations, such as, for example, low signal generation and template independent cleavage and signal generation.

Thus, while reducing the present invention to practice, the inventors experimented with various oligonucleotide probe configurations in efforts to traverse the limitations inherent to the oligonucleotide probes described hereinabove and in U.S. Pat. No. 5,451,503.

As is further described in Examples 3–6 below, the experimentation conducted by the inventors of the present invention yielded novel probe configurations which (i) enable to substantially reduce template independent cleavage; (ii) reduce the reaction order; and (iii) allow for template recycling and signal amplification.

Thus, according to a presently preferred aspect of the present invention, and as specifically described in Example 6 of the Examples section which follows (see the "Looped probe variants" and "Blocked probes" sections), there is provided a single oligonucleotide or a bi-molecular oligonucleotide probe (oligonucleotide system or assembly) which are configured so as to form a first duplex structure devoid of the nucleic acid cleaving agent recognition sequence when not hybridized with the target nucleic acid sequence, while following hybridization form a second duplex structure which includes a nucleic acid cleaving agent recognition sequence.

This feature of this aspect of the present invention is enabled by designing the probe such that following hybridization with the target sequence, the first duplex structure is less favored energetically then a second duplex structure. This ensures that the first duplex structure is only formed in the absence of the target nucleic acid sequence. As is further detailed and exemplified in Example 6, the formation of this first duplex structure which is devoid of the nucleic acid cleaving agent recognition sequence substantially reduces background signal generated by target independent duplex and cleavage site formation which can occur when utilizing the probes described in, for example, U.S. Pat. No. 5,451,503.

As is further detailed in Examples 3–4 of the Examples section which follows, a preferred bimolecular oligonucleotide probe of the present invention, is configured such that template hybridization of a first oligonucleotide member of the bimolecular probe is dependent on preceding template hybridization of a second oligonucleotide member of the bimolecular probe which preferably serves as a non recycled or permanent anchor.

As such, and according to another presently preferred aspect of the present invention, there is provided a bi-molecular probe which is configured such that the target complementary region of one of its oligonucleotide members is selected so as to allow hybridization thereof only following hybridization of the other oligonucleotide member to the target, to thereby reduce the overall reaction order by a single unit or close to a single unit. It will be appreciated in this respect that the oligonucleotide that is selected to stably hybridize with the target is recycled along with the target. No further hybridization/dissociation thereof is required to maintain hybridization/dissociation of the other oligonucleotide and thereby the reaction order is reduced, its specificity increased and the signal generated is amplified. In addition, such a configuration reduced to a great extent single stranded target depletion due to target reassociation.

According to a preferred embodiment of the present invention, the bi-molecular probe is designed such that following hybridization of both oligonucleotide members, only the first oligonucleotide member of the bi-molecular oligonucleotide probe is cleaved by the cleaving agent (see SpltRE and ModRE/MutRE of Example 3). As a result of this cleavage, only this oligonucleotide member is dissociated from the template while the other uncleaved oligonucleotide member remains anchored to the template and is recycled therewith so as to effect reaction order reduction.

Preferably, in this case, the target complementary region of the non-cleavable oligonucleotide member is selected having a melting temperature higher than that of the cleavable oligonucleotide member so as to allow this member to remain hybridized with the template following dissociation of the first oligonucleotide member.

Figure 1:
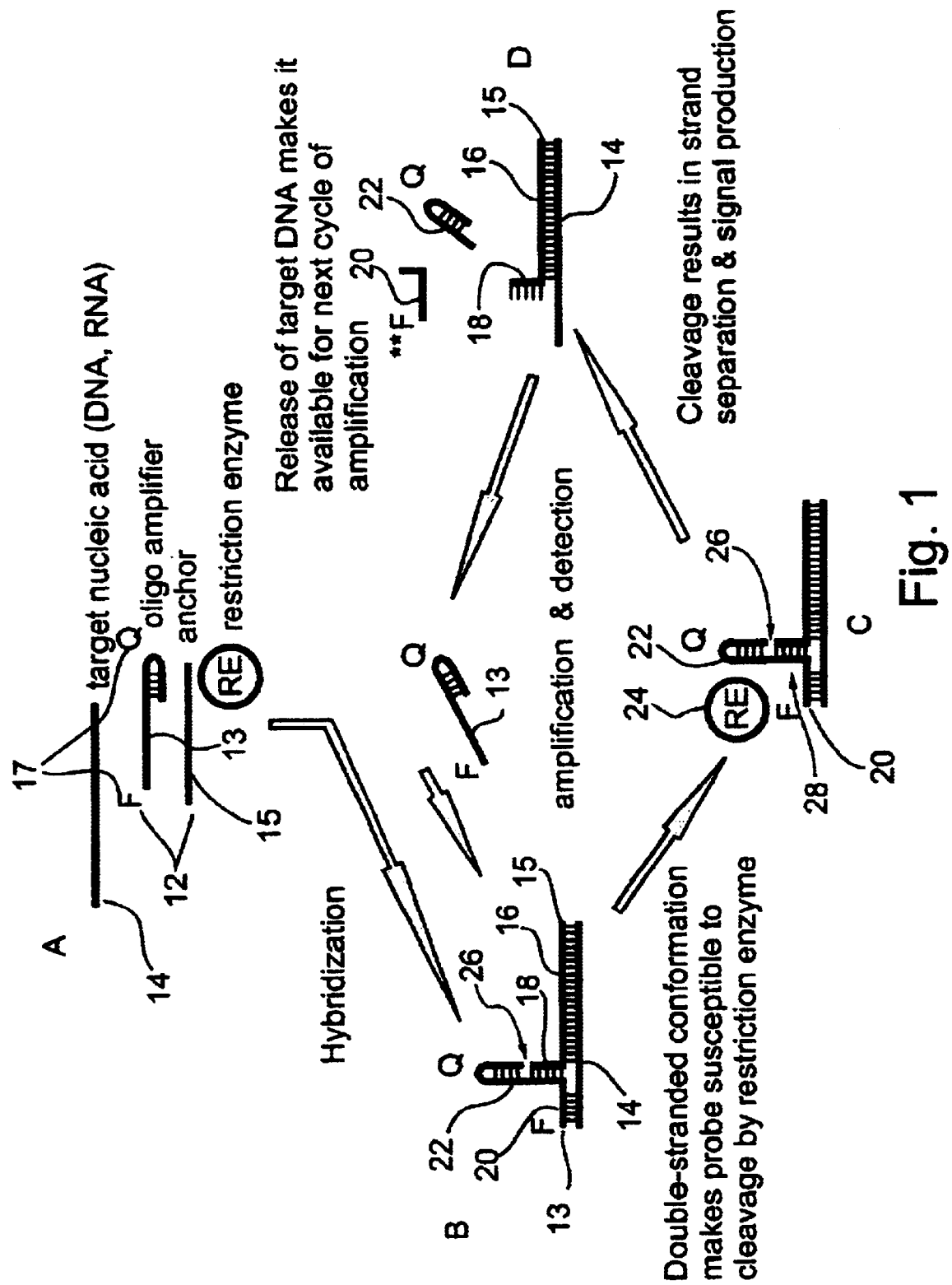

To enable single member cleavage, the bi-molecular oligonucleotide assemblies of the present invention can be configured such that a portion of the duplex structure is formed by self annealing of a portion of the cleavable oligonucleotide member which does not participate in target hybridization (see FIG. 1). The portion of the duplex structure formed can then include at least a portion of the cleaving agent recognition sequence thus allowing cleavage of only the oligonucleotide of the bi-molecular oligonucleotide assembly which forms such self annealing while the other oligonucleotide serves as an anchor similar to that described hereinabove. In this case, the cleavable duplex is designed to include a nick replacing one of the internucleotidic bonds cleavable by the cleaving agent.

Alternatively, the cleaving agent recognition sequence in the non-cleavable oligonucleotide can include at least one modified nucleotide or internucleotidic bond, thus blocking cleavage of a desired strand of the duplex.

Still alternatively, an endonuclease characterized by single strand nicking activity of double stranded DNA (as opposed to complete, double nick restriction activity) can be employed, provided that the oligonucleotides include the appropriate recognition sequence. An examples of such an endonuclease is N.BstNBI distributed by New England Biolabs.

For example, any one of several modificants some of which are further listed hereinbelow can be employed either during or following synthesis of the oligonucleotide so as to construct a cleaving agent recognition sequence which is recognized by a specific cleaving agent but which is cleaved in only one strand of the duplex. In the case of an endonuclease cleaving agent, the recognition sequence of the uncleavable strand can include methylation or acetylation on one or more of the nucleotides included within the recognition sequence, such that a specific endonuclease recognizes and binds with the double stranded recognition sequence but only cleaves (nicks) the unmodified strand.

In another embodiment of the present invention the reaction order of a bi-molecular oligonucleotide probe is maintained, however, the oligonucleotide members of the probe are selected so as to, a great extent, reduce a level of bi-molecular interactions between the oligonucleotide members between themselves or any of the members and the target nucleic acid sequence. As a result, both the level of background is significantly reduced and template recycling following cleavage is also achieved, resulting in far improved and specific detection.

The following paragraphs describe several aspects of the present invention which are clearly distinct from and are clearly advantageous over the prior art, U.S. Pat. No. 5,451,503, in particular, in that each provides (i) signal amplification by reducing reaction order; (ii) signal amplification by template recycling; and/or (iii) reduced background by prevention of template independent cleavage.

Thus, according to one aspect of the present invention there is provided an oligonucleotide or assembly of oligonucleotides useful in detecting a presence or an absence of a target nucleic acid sequence in a sample. The oligonucleotide or assembly of oligonucleotides according to this aspect of the present invention comprising a first region and a second region. At least a portion of the first region and at least a portion of the second region each is capable of hybridizing under predetermined hybridization conditions with the target nucleic acid sequence. The oligonucleotide or assembly of oligonucleotides according to this aspect of the present invention further comprising a third region and a fourth region. The third region and the fourth region being linked to the first region and the second region, respectively. A first portion and a second portion of the oligonucleotide or assembly of oligonucleotides are selected capable of forming a first duplex structure therebetween under the predetermined hybridization conditions. Preferably, the first portion and the second portion of the oligonucleotide or assembly of oligonucleotides are capable of forming the first duplex structure therebetween under the predetermined hybridization conditions are derived from the third and forth regions, respectively. In any case, the first, second, third and fourth regions of the oligonucleotide or assembly of oligonucleotides of this aspect of the present invention are selected such that upon hybridization under the predetermined hybridization conditions of the first region and the second region with the target nucleic acid sequence, the first duplex structure dissociates and a portion of the third region and a portion of the fourth region form a second duplex structure therebetween. The second duplex structure includes a nucleic acid cleaving agent recognition sequence which is absent from the first duplex structure and which, when cleaved, indicates hybridization of the oligonucleotide or assembly of oligonucleotides to the target nucleic acid sequence and therefore indicates the presence of the target nucleic acid in the sample. As a result, background signal associated with template independent cleavage is reduced to a great extent. In a preferred embodiment of this aspect of the present invention the first, second, third and fourth regions of the oligonucleotide or assembly of oligonucleotides are further selected such that following cleavage of the nucleic acid cleaving agent recognition sequence, the first and second regions dissociate from the target nucleic acid sequence, thereby enabling recycling of the target nucleic acid sequence and signal amplification.

According to another aspect of the present invention there is provided an oligonucleotide system useful for detecting a presence or an absence of a target nucleic acid sequence in a sample. The oligonucleotide system according to this aspect of the invention comprising at least a first oligonucleotide and a second oligonucleotide, each of which includes a first region capable of hybridizing with the target nucleic acid sequence under predetermined hybridization conditions. Each of the first oligonucleotide and the second oligonucleotide further includes a second region, wherein upon hybridization, at least a portion of the second regions of the first and second oligonucleotides form a duplex structure which includes a nucleic acid cleaving agent recognition sequence, whereby the second regions of the first oligonucleotide and the second oligonucleotide are selected such that in the presence of a nucleic acid cleaving agent recognizing the nucleic acid cleaving agent recognition sequence, only the first oligonucleotide is cleavable by the nucleic acid cleaving agent. In this case, selecting the second oligonucleotide having sufficient stability to hybridize with the target nucleic acid sequence in the absence of the first oligonucleotide would result in reduction of the reaction order, contributing to an increase in signal formation. Thus, preferably, the first and second regions of the first and second oligonucleotides are selected such that upon cleavage of the first oligonucleotide, the first region of the first oligonucleotide dissociates from the target nucleic acid sequence. Still preferably, the first region of the second oligonucleotide is selected such that under the predetermined hybridization conditions and following dissociation of the first oligonucleotide, the first region of the second oligonucleotide remains hybridized to the target nucleic acid sequence, thereby allowing recycling of the target nucleic acid sequence with respect to the first oligonucleotide.

According to yet an additional aspect of the present invention there is provided an oligonucleotide system useful for detecting a presence or an absence of a target nucleic acid sequence in a sample. The oligonucleotide system comprising at least a first oligonucleotide and a second oligonucleotide, each of which includes a first region which is complementary or substantially complementary to the target nucleic acid sequence and each of which further includes a second region, the second regions are complementary or substantially complementary and are selected such that upon annealing therebetween they form a duplex structure which includes a nucleic acid cleaving agent recognition sequence, whereby under predetermined hybridization conditions the first region of the first oligonucleotide is stably hybridizable with the target nucleic acid sequence only if the first region of the second oligonucleotide is stably hybridizable with the nucleic acid target sequence, to thereby reduce the reaction order, reduce the background signal and increase the specificity. Template recycling is enabled in this case by selecting the other oligonucleotide such that following restriction thereof, it is released from the target. Preferably, under the predetermined hybridization conditions the second regions of the first and second oligonucleotides are substantially non-hybridizable with one another per se, so as to further reduce the background signal. Still preferably, the second regions of the first oligonucleotide and the second oligonucleotide are selected such that in the presence of a nucleic acid cleaving agent recognizing the nucleic acid cleaving agent recognizing sequence, only the first oligonucleotide is cleavable by the nucleic acid cleaving agent. Advantageously, the first and second regions of the first and second oligonucleotides are selected such that under the predetermined hybridization conditions and upon cleavage of the first oligonucleotide, the first region of the first oligonucleotide dissociates from the target nucleic acid sequence. Still advantageously, at least one nucleotide or internucleotidic bond of the second oligonucleotide which forms a part of the nucleic acid cleaving agent recognition sequence is a modified or analogous nucleotide or internucleotidic bond, selected so as to prevent cleavage of the second oligonucleotide by the nucleic acid cleaving agent. Optionally, the duplex structure is formed in part by self annealing of a portion of the second region of the first oligonucleotide. Preferably, the second regions of the first and second oligonucleotides are selected such that the nucleic acid cleaving agent recognition sequence is characterized by a nick replacing an internucleotidic bond cleavable by the nucleic acid cleaving agent.

According to yet a further aspect of the present invention there is provided an oligonucleotide system useful for detecting a presence or an absence of a target nucleic acid sequence in a sample. The oligonucleotide system comprising at least a first oligonucleotide and a second oligonucleotide, each of which includes a first region selected complementary or substantially complementary to the target nucleic acid sequence and each of which further includes a second region, the second regions are complementary or substantially complementary and are selected such that upon annealing therebetween the second regions from a duplex structure which includes a nucleic acid cleaving agent recognition sequence, whereby under predetermined hybridization conditions the first regions of the first oligonucleotide and the second oligonucleotide are stably hybridizable with the target nucleic acid sequence, and the second regions of the first oligonucleotide and the second oligonucleotide are stably hybridizable therebetween only when the first oligonucleotide, the second oligonucleotide and the target nucleic acid sequence are co-annealed, so as to allow template recycling and background signal reduction.

The general principle of a target nucleic acid detection method according to one preferred aspect of the present invention is exemplified by FIG. 1.

In a first step (marked as A), oligonucleotides 13 and 15 of oligonucleotide system 12 are incubated with a target nucleic acid sequence 14 under predetermined hybridization conditions. Oligonucleotide 13 includes a fluorescer-quencher pair 17 which when separated beyond a non-interacting distance lead to the generation of a detectable signal.

In a second step (marked as B), hybridization between oligonucleotides 13 and 15 and target 14 takes place. Such hybridization can be either sequential or simultaneous depending on the sequence and length of each region of oligonucleotides 13 and 15. For example, regions 16 and 18, of oligonucleotide 15 and regions 20 and 22 of oligonucleotide 13 can be selected such that hybridization of region 20 to target 14 is dependent upon preceding hybridization of region 16 to target 14.

In any case, in a third step (as indicated by C), the duplex structure including a cleaving agent recognition sequence, which according to this aspect is formed in part by self annealing of region 22 of oligonucleotide 13 and is thus nicked on one strand (as indicated by 26), is cleaved by a cleaving agent 24 (further described hereinbelow). Thus, only region 22 is cleaved by cleaving agent 24 (indicated by 28) leading to the release of a portion of region 22 and subsequent dissociation of region 20 from target 14.

As a result of the cleavage, region 22 is separated from region 20 thus leading to the separation between the fluorescer and quencher and the generation of a detectable signal.

Since oligonucleotide 15 is not cleaved and since it remains hybridized to target 14 it therefor recycles therewith, thus reducing the reaction order of the target nucleic acid detection method according to this aspect of the present invention.

As is shown in FIG. 1, according to a presently preferred embodiment of the present invention, for any of its aspects, all reaction ingredients are premixed as opposed to their stepwise addition. In some embodiments this calls for heat stability of the restriction enzyme employed, such as Bstb1 or Taq1.

Thus, the above described aspects of the present invention provide oligonucleotide probes or assemblies which are useful in detection of target sequences and yet are devoid of the limitation inherent to prior art oligonucleotide probes such as those described in U.S. Pat. No. 5,451,503.

According to one preferred embodiment of the present invention the cleaving agent is a chemical agent.

According to another preferred embodiment of the present invention the cleaving agent is a nuclease inhibiting but not limited to, an endonuclease, an exonuclease or a ribonuclease. Preferably the nuclease is selected thermostable such that it can be used in the temperature range used for oligonucleotide-target sequence hybridization.

According to another preferred embodiment of the present invention the nuclease is an endonuclease capable of recognizing and cleaving a recognition sequence, formed by for example, a DNA-DNA or DNA-RNA hybrid.

The recognition sequence is typically a palindromic sequence at least 4 base pairs long and typically not more than 8 base pairs long. Endonucleases which recognize longer stretches of nucleotides or endonucleases which cleave at a site which is remote to the recognition sequence can also be utilized by the present invention. Normally, a specific endonuclease will recognize a specific base pair sequence, bind it to and cleave one or both strands of the duplex nucleic acid sequence depending on the cleaving agent used and the nucleotides forming each stranded of the cleaving agent recognition sequence.

It will be appreciated, however, that several endonucleases exhibit cleaving characteristics which change according to the conditions or concentration of the endonuclease employed. This includes the so called "star" activity of endonucleases, wherein under suboptimal conditions some endonucleases cleave sequences in addition to the specific sequences which are typically cleaved thereby. Thus, endonucleases must be carefully selected, although, as will be appreciated by one ordinarily skilled in the art, at times, sub-optimal/non-recommended conditions are preferred in order to allow concomitant cleavage, hybridization and dissociation.

It will be appreciated that in order to design an oligonucleotide or an assembly of oligonucleotides which form the duplex structure and as such the cleaving agent recognition sequence only when hybridized to the target nucleic acid sequence or sequences, several parameters and considerations must be taken into account. First, oligonucleotides of the present invention must be able to hybridize to a target nucleic acid sequences as hybridization conditions which allow differentiation between nearly identical targets which for example vary in sequence by as little as one nucleotide. Thus, for example, a mutated form of a gene containing a single point mutation can be differential and detected. Second, at least some of the oligonucleotides must be synthesized with target hybridizing regions which are long enough to allow hybridization but yet short enough to dissociate from target following cleavage of the stem and to minimize overall complexity of the molecule and as such the chances of undesirable secondary structures formation. In addition, the target-specific arms should not contain a cleaving agent recognition site. Third, the regions which are responsible for the duplex structure formation must be designed in both the single oligonucleotide and the assembly of oligonucleotides such that the duplex structure is formed substantially only or preferably following hybridization of the oligonucleotide to the assembly of oligonucleotides to the target nucleic acid sequence. Otherwise a high background signal resultant from cleavage of target non-hybridized oligonucleotides will be produced. Furthermore, the cleavage recognition sequence must be chosen in accordance with preferred assay conditions and length of stem. In addition, the stem should not interact with the target specific arms. These and other considerations are further discussed in detail in the Examples section that follows.

The oligonucleotide or the assembly of oligonucleotides of the present invention can be DNA, RNA or PNA, or chimeric mixtures or derivatives or modified versions thereof, so long as it is still capable of hybridizing to the target nucleic acid sequence, and still capable of forming a nucleic acid cleaving agent recognition sequence cleavable in at least one strand by the cleaving agent. The oligonucleotides can be modified at the base moiety, sugar moiety, or phosphate backbone, and may include other appending groups or labels, so long as it is still capable of functioning as a detecting oligonucleotide according to the teachings of the present invention. In addition, an oligonucleotide may also include non-hybridizing moieties interposed between hybridizing moieties thereof.

Thus, an oligonucleotide according to the present invention includes nucleotides or nucleotide analogs hybridizable with the naturally occurring nucleobases and in addition may also include non-hybridizing moieties.

For example, the oligonucleotide or assembly of oligonucleotides may comprise at least one modified base moiety such as, but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

Examples of modified sugar moieties incorporatable into the oligonucleotide or the assembly of oligonucleotides of the present invention include but are not limited to, arabinose, 2-fluoroarabinose, xylulose, and hexose.

Examples of modified phosphate backbone incorporatable into the oligonucleotide or the assembly of oligonucleotides of the present invention include but are not limited to, a phosphorothioate, a phosphorodithioate, a phosphoramidothioate, a phosphoramidate, a phosphordiamidate, a methylphosphonate, an alkyl phosphotriester, and a formacetal or analog thereof.

The oligonucleotides or the assembly of oligonucleotides of the present invention may be derived by standard methods known in the art, e.g., by de novo chemical synthesis of polynucleotides using an automated DNA synthesizer (such as is commercially available from Biosearch, Applied Biosystems, etc.) and standard phosphoramidite chemistry.

A preferable method for synthesizing oligonucleotides is conducted using an automated DNA synthesizer by methods known in the art. As examples, phosphorothioate oligonucleotides may be synthesized by the method of Stein et al. (1988, Nucl. Acids Res. 16:3209–3221), methylphosphonate oligonucleotides can be prepared by use of controlled pore glass polymer supports (Sarin et al., 1988, Proc. Natl. Acad. Sci. U.S.A. 85:7448–7451), etc. Once the desired oligonucleotide is synthesized, it is cleaved from the solid support on which it was synthesized and treated, by methods known in the art, to remove any protecting groups present. The oligonucleotides may then be purified by any method known in the art, including extraction, gel purification and column chromatography. The concentration of the synthesized oligonucleotide can then be verified by methods well known in the art.

It will be appreciated that the oligonucleotides of the present invention can also be linked to a solid support either following synthesis or by directly synthesizing the oligonucleotides on an appropriate solid support. It will be appreciated that when linked to a solid support the oligonucleotides preferably include a spacer such that a linked oligonucleotide or an assembly of linked oligonucleotides can function as described hereinabove without suffering from spatial limitations, which can limit the oligonucleotides from hybridizing to a target nucleic acid sequence and forming the intrinsic duplex structure.

As already mentioned hereinabove, the oligonucleotide or the assembly of oligonucleotides according to the present invention preferably include at lest one detection moiety linked to the oligonucleotide or the assembly of oligonucleotides in a manner so as to enable detection of the separation of the region or regions of the oligonucleotide or assembly of oligonucleotides.

Oligonucleotides of the invention may be labeled with moieties during chemical synthesis of the oligonucleotide or the label may be attached after synthesis by methods known in the art.

According to one preferred embodiment of the present invention a detection moiety is a directly detectable detection moiety or indirectly detectable detection moiety. Examples of directly detectable detection moieties include a radioactive ion, such as $^{32}P$, $^{35}S$, $^{3}H$, and the like, or a fluorescer (examples of fluorescers are listed hereinbelow). In this case, cleavage can be detected by simply monitoring the formation and accumulation of cleavage products via various fractionation techniques or chromatography and electrophoresis techniques which can include for example, column chromatography, gel chromatography or gel electrophoresis.

Examples of indirectly detectable detection moieties include members of binding and/or chemically interacting pairs such as, but are not limited to, an antibody, an antigen, an epitope, a ligand, a receptor, an ion, a chelator, and the like. These detection moiety types can also be detected using chromatography or electrophoresis but produce detectable signals only when a particular chemical reaction is conducted, such as an enzymatic reaction. Such detection moieties are preferably selected heat stable, so as to survive the denaturing and hybridization steps of the detection reaction. For example, an oligonucleotide may be indirectly labeled by incorporating therein a nucleotide covalently linked to a hapten or to a molecule such as biotin, to which a labeled avidin molecule may be bound, or digoxygenin, to which a labeled anti-digoxygenin antibody may be bound. As is further exemplified in the Examples section that follows, and while reducing the present invention to practice, a biotin labeled oligonucleotide was detected via a streptavidin conjugated enzyme by using conventional gel electrophoresis.

In addition, indirectly detectable moieties can also be used in affinity columns in which a hybridized oligonucleotide-target sequence bound to the column is only released upon cleavage. Such oligonucleotides are labeled during or following synthesis as mentioned hereinabove.

According to a preferred embodiment of the present invention an oligonucleotide or an assembly of oligonucleotides can also be labeled with at least one pair of reasonably interacting detection moieties. For example, a first detection moiety and a second detection moiety of a pair can each be linked to an oligonucleotide or an assembly of oligonucleotides flanking the cleavage recognition sequence, such that upon cleavage of the recognition sequence by the cleaving agent separation of these moieties occurs. The detection moieties are selected such that at least one of these moieties is capable of producing a detectable signal when separated to a non-interacting distance from the other detection moiety.

Examples of resonantly interacting pairs of detection moieties which can be used while implementing the present invention, include, but are not limited to, a fluorescer and a quencher and any other type of fluorescent resonant energy transfer (FRET) pairs (for reference, see for example "Fluoroscence resonance energy transfer" by Paul R. Selvin, 1995, Methods in Enzymol. Vol 246, Chap. 13, pp. 300; and "Handbook of fluorescent probes and research chemicals" by Richard P. Haugland, sixth ed. Molecular probes. Specific examples of molecules which can be used in fluorescent resonant energy transfer are listed hereinbelow.

The optimal distance between a first and a second detection moieties of a pair when linked to the oligonucleotide probe will be that distance wherein the emissions of the first moiety are absorbed by the second moiety. This optimal distance varies with the specific molecules used, and is defined by Forster Radius. Forster Radius (Ro) is the distance between a donor and acceptor that allows quenching of 50% of the excited donor molecules by the quencher. Ro may be defined for any given FRET pair, and may be used as the guideline for designing a FRET-labeled probe.

One of ordinary skill in the art can easily determine, using art-known techniques of spectrophotometry, which fluorophores will make suitable donor-acceptor FRET pairs. For example, FAM (which has an emission maximum of 525 nm) is a suitable donor for TAMRA, ROX, and R6G (all of which have an excitation maximum of 514 nm) in a FRET pair. Additional examples to moieties which can be used include but are not limited to, 4-acetamido-4'-isothiocyanatostilbene-2,2'-disulfonic acid acridine and derivatives such as, acridine, acridine isothiocyanate, 5-(2'-aminoethyl)aminonaphthalene-1-sulfonic acid (EDANS), 4-amino-N-_13-vinylsulfonyl)phenyl!naphthalimide-3,5, disulfonate (Lucifer Yellow VS), N-(4-anilino-1-naphthyl) maleimide, anthranilamide and Brilliant Yellow; coumarin and derivatives such as, coumarin, 7-amino-4-methylcoumarin (AMC, Coumarin 120), 7-amino-4-trifluoromethylcouluarin (Coumaran 151), cyanosine 4',6-diaminidino-2-phenylindole (DAPI), 5', 5"-dibromopyrogallolsulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-dimethylamino naphthalene-1-sulfonyl chloride (DNS, dansyl chloride), 4-(4'-dimethylaminophenylazo)benzoic acid (DABCYL) and 4-dimethylaminophenylazophenyl-4'-isothiocyanate (DABITC); eosin and derivatives such as, eosin and eosin isothiocyanate; erythrosin and derivatives such as, erythrosin B and erythrosin isothiocyanate ethidium; fluorescein and derivatives: such as, 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate, QFITC (XRITC), fluorescamine, IR144, IR1446, Malachite Green isothiocyanate, 4-methylumbelliferone, ortho cresolphthalein, nitrotyrosine, pararonsaniline, Phenol Red, B-phycoerythrin and o-phthaldialdehyde; pyrene and derivatives such as, pyrene, pyrene butyrate, succinimidyl 1-pyrene butyrate and Reactive Red 4 (Cibacron R. T. Brilliant Red 3B-A); rhodamine and derivatives such as, 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101, sulforhodamine 101, (Texas Red), N,N, N',N'-tetramethyl-6-carboxyrhodamine (TAMRA), tetramethyl rhodamine, tetramethyl rhodamine isothiocyanate (TRITC), riboflavin, rosolic acid and terbium chelate derivatives.

Oligonucleotides are preferably modified during synthesis, such that a modified T-base is introduced into a designated position by the use of Amino-Modifier C6 dT (Glen Research), and a primary amino group is incorporated on the modified T-base, as described by Ju et al. (1995, Proc. Natl. Acad. Sci., USA 92:4347–4351). These modifications may be used for subsequent incorporation of fluorescent dyes into designated positions of the oligonucleotides.

It will be appreciated that although the use of a single detection moiety or a pair of detection moieties for detection of the separation resultant from the cleavage is preferred by the present invention, such detection can also be effected in oligonucleotides and assemblies of oligonucleotides which are untagged by such moieties. In this case the resultant cleavage products can be specifically detected by various chromatographic techniques such as HPLC and the like or electrophoretic techniques.

Thus, the present invention provides oligonucleotides and assemblies of oligonucleotides which are useful in methods for nucleic acid target detection. The oligonucleotides of the present invention are particularly advantageous over prior art designs for target sequence detection in that following the production of a detectable signal the oligonucleotides of the present invention or portions thereof dissociate from the target nucleic acid. This dissociation allows additional oligonucleotides to hybridize with the target and to subsequently produce additional detectable signals. Thus, if excess amounts of oligonucleotides are used, target recycling is enabled and signal amplification generated.

In addition, the oligonucleotides or assembly of oligonucleotides described hereinabove are advantageous over prior art designs in that they substantially reduce background signals associated with target independent cleavage.

Furthermore, since restriction and thus generation of a signal is independent of the type and sequence of the target polynucleotide the oligonucleotide probes of the present invention can include a universal structure at the cleavage region which facilitates their synthesis and applicability. An added benefit to target independent cleavage is that the probes of the present invention can be used to detect both DNA and RNA target sequences.

Finally, since the present invention is an isothermal procedure, it facilitates detection of target sequences via an easy and relatively inexpensive procedure.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sandbrook et al., (1989); "Current Protocols in Molecular Biology" Volumes I–III Ausubel, R. M., et ed. (1994); Cell Biology: A Laboratory Handbook" Volumes I–III Cellis, J. E., ed. (1994); "Current Protocols in Immunology" Volumes I–III Coligan J. E., ed. (1994); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317 Academic Press.

Example 1

Materials and General Methods

Oligonucleotides:

Following careful design, the oligonucleotides and oligonucleotide assemblies described hereinbelow were acquired from Biotechnology General Ltd., Israel or Genset, France. The prediction of structure and thermodynamic stability of the oligonucleotides, at different assay conditions, was performed using the Gene runner software, version 3.00. FIG. 2 summarizes the secondary structures and features of all of the oligonucleotides synthesized and tested while reducing the present invention to practice.

PCR reactions:

PCR reactions were conducted using the Programmable Thermal Controller PTC-100™ (MJ Research, Inc.). The DNA utilized as template in the PCR reactions was prepared from whole-cell lysate of human embryo fibroblast (HEF) cells infected with cyto-megalo virus (CMV, ATCC strain AD169).

Restriction Endonucleases and Carrier DNA:

Restriction enzymes used for template DNA and oligonucleotide probes cleavage were purchased from New England BioLabs, Inc., USA. Carrier DNA preparations (tRNA, salmon sperm DNA and human placental DNA) were purchased from Sigma Israel, Ltd.

Hybridization and Cleavage Assays:

Comparative hybridization assays performed at a temperature range of 44° C.–66° C. were conducted in the Stratagene Robocycler/gradient 96 Temperature Cycler. CMV-DNA was incubated with oligonucleotide probe(s) in the presence of 50 to 200 mM NaCl, 10 mM $MgCl_2$ and 10 mM Tris-HCl. Reactions were conducted at pH of 7.8 or 8.5 in a final volume of 25 μl. Concentration of salts, molar ratios of oligonucleotide probe(s) to target DNA and temperature of the assay varied according to the specific requirements of each assay, as is further detailed hereinunder.

For determination of CMV-dependent cleavage of the probe(s), restriction enzymes were added as well. Restriction reactions were stopped using gel-loading buffer containing EDTA, and were stored at 4° C. until electrophoresed. Evaluation of CMV-independent cleavage of the oligonucleotide probes (background cleavage) was performed in the absence of CMV-DNA. As an additional control for CMV-independent cleavage, enzymatic digestion of oligonucleotide probes was attempted in the presence of non-relevant PCR products, tRNA, salmon sperm DNA or human placental DNA. DNA-dependent cleavage of the probe was not detected in any of these negative control experiments. Determination of maximal hybridization efficiency was performed in the absence of enzyme, using non-denaturing gel electrophoresis. The salt concentration was changed to affect both hybridization stringency and enzyme activity.

Assays were conducted at temperatures selected within the range of 44° C. to 66° C. In general, and as shown for the paired-probe (FIG. 3a) and looped probe (FIG. 3b), the temperature of the assay was selected as follows: (i) 5–30° C. higher than the Tm of the oligonucleotide stem (duplex forming region), preferably 10–15° C. higher, so as to allow target-dependent stem-formation; (ii) 10° C. below to 25° C. above the Tm of each of the target-specific arms (target DNA hybridizing regions) of the oligonucleotides probes, preferably 5–10° C. above the Tm of the individual target-specific arms, so as to allow dissociation of probes from the target nucleic acid following enzymatic cleavage; (iii) 0–40° C. below to 5° C. above the Tm of the full-length hybrid, preferably 10–20° C. below, to encourage hybrid formation in the presence of target nucleic acid sequences; and (iv) 25° C. below to 10° C. above the restriction enzyme's optimal temperature, so as to allow between 30–100% enzymatic activity.

Detection:

Reaction products were analyzed by gel electrophoresis in native and urea containing (denaturing) polyacrylamide gels. Gel analysis was conducted using the Xcell™ Minicell gel electrophoresis apparatus using Polyacrylamide purchased from Serva Electrophoresis, GmbH, (Cat. No. 10680). Southern blotting was performed using blotting modules and disposable plastic cassettes (Novex, USA) and Hybond-H+ or NX nylon membranes (Amersham, UK).

For determination of single strand confirmation, samples were boiled prior to loading on gels and 7M urea was added to both the gel and gel-loading buffer. For determination of hybrids and secondary structures, native electrophoresis conditions were employed. Gels were then transferred onto Hybond-N+ or NX nylon membranes and the DNA was immobilized to the membranes by UV irradiation. The membranes were incubated with streptavidin-conjugated alkaline-phosphatase and the biotinylated reactants were then visualized using the BCIP/NBT substrate.

Target Nucleic Acid Sequences:

It will be appreciated that any target nucleic acid sequence is detectable providing a dedicated hybridizable oligonucleotide probe is prepared according to the teachings of the present invention so as to allow its detection.

Homologues of arbitrarily chosen regions of CMV-DNA were detected in the NCBI database using the BLAST algorithm. Homologous sequences were detected in various organisms, including human, pathogens and other organisms. The longest sequences contained 17 base pairs. The melting temperature (Tm) of the CMV-homologous sequence that shared the highest degree of homology with the CMV-DNA was 50° C. The region of the oligonucleotides according to the present invention which is complementary to the target nucleic acid (i.e., the arm) was synthesized to include sequences which are only in part homologous to the CMV homologous sequences mentioned above. This ensured that each arm of the oligonucleotide probe has a lower Tm when hybridized with these non-CMV sequences. Furthermore, each of the two target-specific arms was designed to have Tm values above 50° C. Since the reaction temperature is above 50° C., none of the target-specific arms alone can form a table hybrid with the target-polynucleotide sequence. Since the Tm value of the two arms together is higher than the Tm of each arm alone, and is also higher than the reaction temperature, both arms are needed for hybridization with the double stranded CMV DNA sequence. Therefore, recognition of non-CMV-DNA by a probe that is only partially complementary to these sequences is highly unlikely under the above described assay conditions. Indeed, when human placental DNA or salmon sperm DNA were used as control target DNA instead of CMV-DNA, hybridization of probes to the control DNA was not detected (paired probes) or slightly detected (looped probes), however, in both cases neither the hybridization of the CMV-DNA to the probes nor DNA dependent probe cleavage was substantially affected.

Example 2

Target Nucleic Acids

CMV-DNA Preparations:

A 263 base pair fragment (SEQ ID NO:1) derived from the CMV genome (VRL Accession No. X17403) was used as a template for Various CMV-DNA preparations which were used as a target DNA sequence (FIG. 4). The main features of the various preparations are listed in Table 1 and are further detailed hereinbelow.

PCR amplified double stranded CMV-DNA (p.CMV-263, ds): This unique CMV fragment was amplified using 5'-AGACCTTCATGCAGATCTCC-3' (sense CMV-PCR primer, SEQ ID NO:2) as a sense primer and 5'-GGTGCTCACGCACATTGATC-3' (antisense CMV-PCR primer, SEQ ID NO:3) as an antisense primer, along with a DNA preparation from whole-cell lysate of CMV-infected HEF cells as a PCR template. The PCR reaction included a first denaturing step of 5 minutes at 94° C., followed by thirty cycles of 1 minute at 94° C.; 30 seconds at 58° C.; 30 seconds at 72° C. and a final extension step of 5 minutes at 72° C.

TABLE 1

The main features of various CMV-DNA preparations utilized as a target DNA sequence in oligonucleotide hybridization reactions

| Prep. | Length (bp) | Strand | Synthesis | Designation, and Remarks | SEQ ID NO: |
|---|---|---|---|---|---|
| 1 | 263 | ds | PCR | p.CMV-263.ds | 1 |
| 2 | 263 | ss, antisense | Asymmetric PCR | p.CMV,263.ss Includes a fair amount of ds as well | 4 |

TABLE 1-continued

The main features of various CMV-DNA preparations utilized as a target DNA sequence in oligonucleotide hybridization reactions

| Prep. | Length (bp) | Strand | Synthesis | Designation, and Remarks | SEQ ID NO: |
|---|---|---|---|---|---|
| 3 | 50 | ds | PCR + DdeI | p.CMV-1.ds | 5 |
| 4 | 35 | ds | PCR + HaeIII/Fnu4HI | p.CMV-2.st.ds | 6 |
| 5 | 59 | ds | PCR + HaeIII/AflII | p.CMV-2.lg.ds | 7 |
| 6 | 36 | ss, sense | Seq as for Prep. 3 | sense CMV-2.st Biotinylated at 5'-end | 8 |
| 7 | 36 | ss, antisense | Seq as for Prep. 3 | antisense CMV-2.st | 9 |
| 8 | 36 | ds | Seq as for Prep. 3 | syn. CMV-2st.ds Biotinylated at 5'-end of sense 1:1 mixture of preparations 6 and 7 | 10 |
| 9 | Viral DNA | ds | | g.CMV-1/2.st/2.lg CMV-infected HEF genomic DNA Treated with DdeI; HaeIII + Fnu4HI or HaeIII + AflII | n.a. |

Prep = preparation, ss = single stranded; ds = double standed; n.a. = not applicable PCR amplified single strand antisense CMV-DNA (p.CMV-263.ss): The antisense strand was amplified using the same PCR program, template and primers that were used for amplification of the double stranded DNA, with the exception that the antisense primer was added in 20-fold excess over the sense primer and the PCR program was run for 40 cycles. The final PCR product was enriched with a single stranded CMV antisense strand (263 bp), but contained double stranded DNA (263 bp) as well.

Cleaved PCR amplified double stranded CMV-DNA (p. CMV-1, 2.st, 2.lg, ds): As shown in FIG. 4 the PCR amplified double stranded CMV fragment (263 bp) was digested using either DdeI (preparation 3), HaeIII+Fnu4HI (preparation 4) or AflII+HaeIII (preparation 5) to produce restriction fragments which match the exact sequence hybridizable by the arms of the various oligonucleotide probes. Since these CMV restriction fragments (50, 35 and 61 bp) are considerably shorter than the 263 bp PCR products, the various oligonucleotide probes better competed for the native CMV sense strand for hybridization than the antisense CMV strand, and as such prevented self-annealing of the double stranded CMV-DNA.

Synthetic single stranded and double stranded CMV-DNA (sense/antisense CMV-2 st. and syn. CMV-2 st. ds): Two complementary single stranded CMV-DNA fragments were chemically synthesized. A synthetic biotinylated sense strand (SEQ ID NO:8) and a synthetic complementary non-biotinylated antisense strand (SEQ ID NO:9) were added in equimolar concentrations to yield a synthetic double stranded CMV-fragment (SEQ ID NO:10). These synthetic double stranded DNA sequences were synthesized to match the size of most probe arms. Since the exact concentration of each of the synthetic strands is known, a quantitative measure could be determined for a reaction. In addition, the non-biotinylated antisense strand can be used separately in order to improve probe-DNA hybridization, since the complexity introduced by self-annealing of the two strands of the double stranded CMV-DNA is not a factor. Furthermore, the biotinylated sense strand enabled monitoring of the complexity introduced into a reaction by self-annealing of the two strands of the double stranded CMV-DNA.

Enzymatically digested viral/human DNA mixture (g.CMV-1, 2. st, 2 lg): DNA preparation from whole-cell lysate of CMV-infected human embryo fibroblast (HEF) cells was digested to completion by DdeI, HaeIII+Fnu4HI or HaeI+AflII.

Five main categories of aligonucleotide probes have been designed and studied while reducing the present invention to practice and are referred to herein as the paired probes, the bivalent probes, the single probes, the blocked probes and the ModRE/MutRe probes. FIG. 2 summarizes the main features of these probe categories.

Example 3

Bi-molecular—paired probes

Paired probes=First generation: In paired oligonucleotide probes (bi-molecular oligonucleotide assemblies) each oligonucleotide member of the pair contains an arm which is designed to specifically recognize a portion of the target sequence. However, each arm is preferably selected sufficiently short so as to prohibit the formation of a stable hybrid with the target sequence on its own. The concomitant hybridization of the arms of both oligonucleotide members of the pair to the target DNA allows the formation of a double stranded stem (11–18 bp long) between the two oligonucleotide members. This stem is essential for the stabilization of the hybridization between the arms of both oligonucleotide members and the target DNA. In addition, this stem is designed to provide cleavable restriction sites which are formed as a result of the stem structure formation. The specifics are further detailed hereinbelow.

Effects of stem and arms regions on hybridization of paired probes to CMV-DNA: One picomole (pm) of either both members of three different paired probes (FIGS. 5b, 5c and 5e (pair 1 and 2, and SpltRE, respectively, Table 2), one of which is biotinylated, or of the biotinylated member of different paired probes (FIGS. 5a (biotinylated oligonucleotide member of pair 1 and 2, Table 2) and 5d (biotinylated oligonucleotide member of spltRE, Table 2)) and 500 femtomoles (fm) double stranded CMV-DNA (p.CMV-1.ds for 5a–c, p.CMV-2.lg, for 5d–e, see Table 1 above) were added into 96-well plates. The hybridization assays were conducted at 200 mM NaCl, pH=8.5, at a final volume of 25 µl. Reaction mixtures were covered with mineral oil and the plates were heated to 95° C. for 10 minutes so as to allow strand separation in the Robocycler/gradient 96 Temperature Cycler (Stratagene). The plates were then transferred to a temperature gradient block in which each column of the plates was incubated at a different temperature, starting at 44° C. and ending at 66° C., at 2° C. increments. Following 1 hour incubation, a 10 µl aliquot taken from each sample was analyzed by a 12% polyacrylamide native gel. Biotinylated conformants were visualized as described hereinabove under Example 1. The results are presented in FIGS. 5a–e.

As can clearly be seen in FIGS. 5a–e, hybridization of each paired-probe to CMV-DNA, as is evident by the slow migrating bands, depends on the presence of both oligonucleotide members of the pair in the reaction. Hybridization of a biotinylated oligonucleotide in the absence of its paired oligonucleotide member is not observed even though the Tm of the target-specific arm thereof is far higher than the reaction temperature (e.g., FIGS. 5a and 5d). With the addition of the non-biotinylated oligonucleotide member (FIGS. 5b, 5c and 5e) hybridization is observed, suggesting that stem formation is crucial for hybridization of the oligonucleotide members of the paired probes with the CMV-DNA. In addition, it was observed that for oligonucleotide pairs in which the Tm of the target-specific arms was kept constant, but in which the Tm of the stem region was reduced from 58° C. (FIG. 5b) to 42° C. (FIG. 5c), the efficiency of hybridization at high temperatures was considerably lower. Furthermore, it was observed that elevation of the Tm of the non-biotinylated target-specific arm from 61° C. (FIGS. 5b–c) to 87° c. (FIG. 5e) may compensate for a low stem Tm, and thus enable hybridization even when the Tm value of the stem is as low as 12° C.

TABLE 2

Bi molecudar Paired probes

| Pair No. | Sequence 5'–3' | SEQ ID NO. |
| --- | --- | --- |
| 1 | b-TGGTTATCAGAGGCCGGCTTAAAATTCGAAGGGTTCAC | 11 |
|   | GTGAACCCTTCGAATTCACAGCATCACACTAGTCTCC | 12 |
| 2 | b-TGGTTATCAGAGGCCGCTTAAAATTCGAAGGG | 13 |
|   | CCCTTCGAATTCACAGCATCACACTAGTCTCC | 14 |
| 3 | b-GGCTTGGTTATCAGAGGCCGCTTAAAATTCGAAGGG | 15 |
|   | CCCTTCGAATTCACAGCATCACACTAGTCTCCTCTAA | 16 |
| 4 | b-TGGTTATCAGAGGCCGCTTAAAATTCGAAGGGTTCACGA | 17 |
|   | TCGTGAACCCTTCGAATTCACAGCATCACACTAGTCTCC | 18 |
| spltRE-5' | b-CAGCATCACACTAGTCTCCAGCTAGTTCGACGCGCCACGCGTC | 19 |
| spltRE-3' | GAACTAGCTACTCTAAGACATAGCAGCACAGCACCCGACAGAA CTCACTTAAG | 20 | b = 5'biotinylation

Efficiency of cleavage of various paired-probes at different temperatures: The stem structure of each paired probe of paired probes 1–4 listed in Table 2 was designed to include two restriction sites, one for BstBI and the other for TaqI. Table 3 below summarizes the efficiency of cleavage of the paired-probes 1–4 of Table 2 above at different temperatures by these enzymes. As can clearly be seen, the cleavage efficiency of BstBI and TaqI restriction enzymes increases with longer stems. When the stem region is too long specificity is lost due to template-independent stem formation. However, if the reaction temperature is elevated, stem stabilization again depends on hybridization of the paired-probe to the CMV-DNA template, leading to reduction in template-independent cleavage. Thus, designing probes with shorter stem regions cleavage is CMV-dependent at lower temperatures, increasing the temperature to 65° C., a temperature still optimal for enzyme cleavage, inhibits stem formation for these paired probes, and as such no cleavage is observed. Table 3 also demonstrates the importance of the target-specific arm length. As can be seen, pair 2 is cleaved more efficiently than pair 3 although the two pairs have the same stem. A possible explanation for that is that the shorter arms in pair 2 dissociate more easily from the CMV-DNA following cleavage, thereby allowing better recycling of the target, and higher percentage of intact probe is converted to its cleaved form.

Paired probes—second generation: The design of the second generation of paired probes was aimed to increase the efficiency of CMV-dependent cleavage by either directing the reaction so as to prefer stem formation over stem dissociation or by reducing the number of interactions needed for the formation of double stranded stems or in other words, reducing the reaction order. Thus, the non-biotinylated oligonucleotide member of the paired-probe was elongated to allow permanent hybridization with the target DNA, and the restriction recognition site of this strand was rendered cleavage resistant. Thus, the non-biotinylated oligonucleotide member of the paired-probe should be recycled along with the CMV-DNA to which it is hybridized. Two approaches were tested: split restriction site probes (SpItRE) and modified restriction site probes ("MutRE or ModRE"). In both cases the restriction site was

TABLE 3

Features and cleavage efficiency of four paired probes in the presence or absence of target DNA Efficiency of cleavage of various pairs at different temperatures

| Paired probe | Probe features * | RE | 51° C. | | 56° C. | | 59° C. | | 65° C. | |
|---|---|---|---|---|---|---|---|---|---|---|
| | | | −CMV | +CMV | −CMV | +CMV | −CMV | +CMV | −CMV | +CMV |
| 1 | stem: 16 bp, 55° C. | Bstb1 | 50% | 60% | 50% | 70% | N.D | N.D | 0% | 25% |
| | Arms: b-19 bp, 67° C./19 bp, 58° C. | Taq1 | 30% | 40% | 40% | 50% | N.D | N.D | 10% | 20% |
| 2 | stem: 11 bp, 39° C. | Bstb1 | 10% | 10% | 5% | 30% | 0% | 40% | 0% | 0% |
| | arms: b-19 bp, 67° C./19 bp, 58° C. | Taq1 | 10% | 10% | 10% | 70% | 5% | 30% | 0% | 0% |
| 3 | stem: 11 bp, 39° C. | Bstb1 | 5% | 5% | 0% | 10% | 0% | 0% | 0% | 0% |
| | arms: 23 bp, 75° C. 24 bp, 64° C. | Taq1 | 5% | 5% | 10% | 10% | 5% | 10% | 0% | 0% |
| 4 | stem: 18 bp, 63° C. | Bstb1 | 80% | 80% | 80% | 85% | N.D | N.D | 20% | 40% |
| | arms: 19 bp, 67° C. 19 bp, 58° C. | Taq1 | 50% | 50% | 50% | 60% | N.D | N.D | N.D | N.D | b = 5' biotinylation;
RE = Restriction Enzyme;
B = BstBI;
T = TaqI.

FIG. 6 demonstrates the importance of target-specific arm length. Paired probes 2, 3 or both, each of a concentration of 100 nM were incubated in the presence (+) or absence (−) of approximately 100 nm single stranded enriched CMV-DNA (263 bp). An initial hybridization step was conducted at pH 7.8, 60° C., for 15 minutes, in a volume of 30 μl. Following the initial hybridization step, 0.17 units/μl of BstBI was added to each tube and cleavage was allowed to proceed for 2 hours. Eight μl aliquots were analyzed on a 15% acrylamide-urea gel. Biotinylated fragments were visualized as described under Example 1 above. Length (bp) and Tm (°C.) of stem and arms of pair 2 and 3 are listed in Table 3 above.

As can be seen from FIG. 6, pair 2 was cleaved in the presence of CMV-DNA (lane 2) while pair 3 was cleaved to a much lesser extent (lane 4). However in the presence of pair 3 the cleavage of pair 2 was blocked (lane 6). Thus, it seems that accessibility of pair 2 to the template is blocked by pair 3. Pair 3 inhibits the hybridization of pair 2 to the target DNA due to its longer CMV-specific arm sequence. In addition, recycling of relevant DNA could not occur because cleavage of pair 3 did not result in dissociation of the probe-CMV-DNA hybrid complex. The hybrid was kept intact even after enzymatic cleavage and the accessibility of pair 2 to the DNA was blocked. Thus, temperature recycling and as such signal amplification has clearly been demonstrated with the paired probes designed according to the teachings of the present invention.

flanked by at least five base pairs on each side, so as to allow better contact of the restriction enzymes with their restriction sites, so as to increase cleavage efficiency. The structure of the second generation of paired probes is depicted in FIG. 2.

Split Restriction site probes (SpItRE): In the SpItRE paired probe the 3'-arm of the non-biotinylated oligonucleotide member was elongated to allow permanent hybridization with the target DNA (p.CMV-2.1 g, 41 bases long, Tm=90° C.). The 5'-end of this oligonucleotide member participates in stem formation, but contributes only two of the bases forming the TaqI site (5'-Ga-3'). The other two bases forming the recognition site, including the cleavage site itself (5'-T/C-3'), are missing in this strand. As a result, the non-biotinylated oligonucleotide member serves as an anchor on the target DNA for the biotinylated oligonucleotide member. The rest of the nucleotides that are needed to complete the split restriction site are present on the biotinylated oligonucleotide member. The biotinylated oligonucleotide member contains a CMV specific 5'-arm that is similar in length and Tm to that of the first generation of paired probes (19 base long, Tm=63° C.). This arm is therefore expected to dissociate from the target DNA following enzymatic cleavage. On its 3'-end, the biotinylated oligonucleotide member is designed to fold and create a stable intramolecular hairpin structure (6 base long, Tm=87° C.) that contributes the two bases needed for site recognition by TaqI (5'-T/C-3'). These are the nucleotides that are missing on the 5'-end of the non-biotinylated member of the paired probe. Similar to the first generation of paired probes, the enzyme recognizes and cleaves the full restriction site (5'-T/CGA-3') in a double strand configuration only when the two members of the paired probe hybridize. However, in this case only the biotinylated member of the pair is cleaved, while the non-biotinylated member remains uncleaved and hybridized to the target template. It is therefore expected that the complex of the elongated oligonucleotide hybridized to the target DNA will be recycled by the biotinylated oligonucleotide, when present in excess in the reaction mixture.

Modified restriction site probes (MutRE/ModRe): By introducing a modification at the recognition site of the non-biotinylated half of the paired probe, enzymatic cleavage of the modified strand can be prevented. A 5'-t/CGA-3' to 5'-T/CTA-3' and a 5'-T/CGA-3' to 5'-T/CG($N^6$-methyl)A modifications were introduced on the non-biotinylated oligonucleotide members of paired probes, at the recognition site of TaqI/BstBI to yield 5 MutRE probes (SEQ ID NOs:21–25). Similarly to the SpltRE design, the MutRe paired probe approach benefits from a higher concentration of the reactants throughout the incubation and as such should result in a higher efficiency of product formation.

The two concepts outlined hereinabove (spltRE/ModRE and elongated target specific arm) were tested separately, however both can be co-applied to the same probe. The nature of hybridization of a probe pair to the target DNA and the dissociation of the cleaved biotinylated arm from the DNA, may be studied using a modified/elongated oligonucleotide members of a paired probe. For example, the elongated/modified oligonucleotide member of the paired-probes may be combined with various biotinylated oligonucleotide members having different arm lengths and Tm values. In such combinatorial reactions, hybridization efficiency may be studied either independently (using native gels, as shown, for example, in FIG. 5) or along with cleavage efficiency (using denaturing gels, as shown, for example, in FIG. 6).

Example 4

Second Generation Paired Probes—Experimental Results

The non-biotinylated oligonucleotide member of a paired-probe was elongated to allow permanent hybridization with the target DNA (termed herein anchor primer). The 5'-end of this oligonucleotide member participates in stem formation, but contributes only four out of six bases (5'-CGAA-3') of a BstBI recognition site (5'-TTCGAA-3'). The other two bases forming the recognition site (TT), including the cleavage site itself (T/C) are missing from this strand. As a result, the non-biotinylated oligonucleotide member is a non-cleavable target-hybridized anchor which serves to orient hybridization of the biotinylated oligonucleotide member to the target DNA.

The remaining portion of the recognition sequence is present on the 3'biotinylated oligonucleotide member which contains a CMV specific 5'-arm. This arm is designed so as to dissociate from the target DNA following cleavage. On it's 3'-end, the biotinylated oligonucleotide member is designed to fold and create a stable intramolecular hairpin structure (6 base long, Tm=87° C.) that contributes the two bases needed for site recognition by BstBI (5'-TT-3'). These are the two nucleotides that are missing from the 5'-end of the non-biotinylated member of the paired probe.

Similar to the first generation of paired probes, the restriction endonuclease recognizes and cleaves the full restriction site (5'-TT/CGAA-3') only when the two members of the paired probe hybridize to form the double stranded restriction site. However, in this case only the biotinylated member of the pair is cleaved and released from the target while the non-biotinylated member remains uncleaved and anchored to the target DNA with which it is recycled.

Various anchor (stably hybridized) and amplified primers were synthesized (Genosys England) in order to test the effect of short and long anchor sequences on the accumulation of the cleaved amplifier (Tables 4–5).

TABLE 4

| Primer | Sequence (5' to 3') | |
|---|---|---|
| Target | TTGTATGATGACCA | (SEQ ID NO:42) |
| Long Anchor | CGAATT/GACCTTGTACTCATTACACATTGTTTCCACACAT | (SEQ ID NO:43) |
| Short Anchor | CGAATT/TGACCTTGTACTCATTACACAT | (SEQ ID NO:44) |
| Amplifier 1 | b-TGGTCATCATACAAGCGTCACTA/AATTCGAACGGTTT TTTTCCGTT | (SEQ ID NO:45) |
| Amplifier 2 | b-CATCATACAAGCGTCACTAG/AATTCGAACGTTTTTTT CCGTT | (SEQ ID NO:46) |
| Amplifier 3 | b-ATACAAGCGTCACTAG/AATTCGAACGGTTTTTTTCCGTT | (SEQ ID NO:47) |

Bold sequence represents the stem part of the primer; b = 5' biotinylation.

TABLE 5

| Primer | Orientation | Length(nuc.) | Arm Length |
|---|---|---|---|
| Target | Antisense | 59 | n.r. |
| Long Anchor | Sense | 41 | 35 |
| Short Anchor | Sense | 28 | 22 |
| Amplifier 1 | Sense | 47 | 24 |
| Amplifier 2 | Sense | 43 | 20 |
| Amplifier 3 | Sense | 39 | 16 |

Hybridization Tms between the primers and the target DNA are calculated, n.r. = not relevant The amplification reaction was conducted as described under Example 1 above. Briefly, 50 nM of target DNA, 50 nM of short or long anchor oligonucleotide and 250 nM of each amplified oligonucleotide (primers 1, 2, or 3) were mixed together in reaction buffer (10 mM Tris-HCl, 10 mM $MgCl_2$, 50 mM NaCl, pH 7.9) at a final volume of 30 μ. One drop of mineral oil was added and the temperature was raised to 95° C. for 5 minutes for effecting denaturation. The reaction mixtures were then incubated at 65° C. for 15 minutes, a BstBI restriction enzyme was added to a final concentration of 1 unit/μl and the reaction mixtures were kept under the same conditions for an additional hour. Sample analysis and detection were conducted as described under Example 1. The cleavage products were separated in a 12.5% polyacrylamide gel and blotted onto a membrane (FIG. 11a) which was scanned and analyzed using Kodak Digital Science 1D software; the results are summarized in FIGS. 11b–c.

When using the long anchor, a higher accumulation of the cleavage product is observed with all three amplifiers (FIG. 11a). These results show that the use of a long anchor with a higher arm Tm (19° C. higher than first generation bimolecular probes) leads to a significantly higher amplifier cleavage and dissociation (FIG. 11b). As can be seen in FIG. 11c, the use of the long Anchor has increased cleavage from 2.3 to 6.9 times depending on the amplifier used.

Thus, the second generation bi-molecular probe of the present invention having an anchored uncleavable oligonucleotide member is particularly advantageous for target sequence identification since cleavage and dissociation of only one oligonucleotide member reduces the reaction order thus dramatically increasing reaction cycling rate and therefore signal generation.

Example 5

Recycling in Second Generation Paired Probes—Experimental Results

Recycling level of the second generation paired probes was determined by measuring the amount of product (cleaved-amplifier) molecules accumulated versus the amount of the target molecules present in the reaction. Thus, in order to determine the level of recycling, different concentrations of target DNA (0. 0.5 pM, 5 pM, 50 pM, 500 pM, and 5,000 pM) having the following sequence: 5'-TTGTATGATGACCA-3' (SEQ ID NO:48) were added to a buffered (TrisHCl, 10 mM, pH=7.9) assay solution containing 10 mM $MgCl_2$, 50 mM NaCl and 50 nM of the long anchor oligonucleotide (Tables 4 and 5). The resulting reaction mixtures were preheated at 95° C. for five minutes and thereafter incubated at 65° C. for ten minutes so as to allow for saturation by hybridization of the target DNA with the anchor oligonucleotide. Then, amplifier 1 oligonucleotide (Table 4 and 5) was added to each reaction at a final concentration of 250 nM and incubation was continued for additional 15 minutes thus completing a tri-molecular target-anchor-amplifier hybridization. BstBI endonuclease was added to reaction at a final concentration of 1 unit/μl. The samples were incubated for an additional hour so as to allow cleavage of the amplifier oligonucleotide.

Samples containing known amounts of a biotinylated oligonucleotide fragment, identical in length and sequence to the cleavage product of the amplifier (biotin-5'-TTTCATCATAAAAGCGTCACTAGAATT-3' (SEQ ID NO;49) were electrophoresed through a 15% denaturing polyacrylamide gel in the presence of urea and served to create a standard curve. Four μl samples (containing 0, 2 amol, 20 amol, 200 amol, 2 fmol and 20 fmol of target, FIG. 12, insert) were co-electrophoresed therewith. The gel was blotted onto a nylon membrane and detection of biotin was as described under Example 1. The blot was then scanned and analyzed using the Kodak Digital Science ID software. Based on the results, an amplification factor was calculated as the molar ratio between product and target. The amplification factors calculated for each of the target concentrations are shown in FIG. 12. About 50 fmol of product was detected with as little as 20 amol of target-DNA, showing about 2,500-fold amplification. The results shown in FIG. 12 prove that recycling of target DNA indeed occurs in a wide range of target concentrations.

Example 6

Single Molecular Probes:

Single probes-First generation: In order to reduce the number of interactions needed for the formation of a double stranded stem, single molecule oligonucleotide probes (Table 6, FIG. 2) were designed. In single molecule probes the stem is formed by intramolecular interactions. The first set of single molecule probes recognized a sequence of 32–43 nucleotides on the CMV (each arm 16–23 base long) and had stems 10–16 bp long.

TABLE 6

Single molecule probes

| No. | Sequence 5'–3' | SEQ ID NO: |
|---|---|---|
| 1 | b-TTATCAGAGGCCGCTTGAAAATTCGAATTGACCAAGAATTCGAA TTCACAGCATCACACTAGTC | 26 |
| 2 | b-GTTATCAGAGGCCACTTGAAAATTCGAATTGACCAAGAATTCGA ATTCACAGCATCACACTAGTC | 27 |
| 3 | b-TGGTTATCAGAGGCCGCTTGTTATAATCGAATAAATGGAGGAAG ATTAATCGAATATAAGCCAGCATCACACTAGTCTCCTC | 28 |
| 4 | b-TGGTTATCAGAGGCCGCTTGTTATATTCGAATAAATGACCGAGGA GGAAGATTAATTCGAATATAAGCCAGCATCACACTAGTCTCCTC | 29 | b = 5' biotinylation

The Tm of the stem or arm regions of the various single molecule probes was modified by the introduction of mismatches into these sequences, so as to render them "substantially complementary". However, the Tm of the stem was too high in all cases (Tm=65–92° C.) and resulted in high background cleavage of the free probe in the absence of target DNA.

Computer analysis of the target DNA sequence recognized by the first generation of single molecule probes suggested that this particular sequence might be unsuitable for this type of single molecule probes. First, the CMV-specific arms of the probe tend to form dimers. Second, the selected target sequence dictates a high Tm (Tm=82° C.) which encourage self-annealing of the ds target DNA. Finally, the primary structure of the single stranded target DNA enabled a stable self-folded configuration that could interfere with probe hybridization.

As shown in FIG. 7, to test the ability of the first generation single molecule probes to detect a target DNA template the single molecule probe 1 (Table 6) was incubated at 55° C. in 600 mM NaCl in the presence (+, lanes 1–3) and absence (−, lanes 4–6) of p.CMV-1.ss (single stranded enriched, 263 bp, see Table 1 above). The reaction mixtures were incubated for 15 minutes, following which the reaction mixtures were diluted to a final concentration of 100 mM NaCl, 100 nM probe and 42 nM single stranded enriched CMV-DNA (263). Following dilution, either TaqI (T) or BstBI (B) were added to a final concentration of 0.17 units/µl and enzymatic restrictions were allowed to proceed for 2 hours at 65° C. Thereafter, aliquots of 12 µl were taken for denaturing gel analysis. In addition, hybridization reactions (H) were incubated for 2 hours at 55° C. and 600 mM NaCl, in the absence of restriction enzymes, and 2 µl aliquots of which were also analyzed on 8% native gel. In both cases, the visualization of biotinylated fragments was conducted as described under Example 1.

The results are presented in FIG. 7. As is clearly evident, a considerable portion of the probe was cleaved in the absence of CMV-DNA. Furthermore, the presence of target DNA did not increase of the cleavage efficiency, suggesting that the formation of a stable stem was independent of target DNA hybridization for this probe type. However, the reduction of the hybrid concentration upon addition of enzymes suggests that the hybrid may serve as a substrate for the enzymes.

Looped probes: Based on the results obtained from the first generation of single molecule probes, a second generation of single molecule probes was designed. In these probes the intramolecular stem formation in the absence of target DNA is considerably reduced. FIG. 2 depicts the structure of a hybridized second generation looped probe.

The stems of the second-generation single molecule probes were designed to have a lower Tm and a higher accessibility to the enzymes as compared to the stems of the first generation single molecule probes. In these probes, only a four to six base pair sequence of the stem region forms a true double helix. These base pairs include the recognition site of TaqI (T/CGA) (in the case of the six bp the 4-bp RE-site is flanked by a single base pair on each side). The true double helix region of this stem was flanked by pseudo double helix (base pairing between either C-A or G-T rather than G-C and A-T as in normal double helix). The length of the whole stem (sum of both real and pseudo double helices) was calculated to be long enough (15 bp) to enable the probe to serve as a substrate for TaqI. The Tm of the stem was manipulated by changing the length of a poly-A loop formed upon stem formation. The six looped probe variants varied in the size of the pseudo double helix, the size of the poly A loop (4–21 base long), the Tm of the stem region (Tm= 44–53° C.) and overall stem length (10–15 base long).

In addition to the changes in the stem region, the target sequence for these new probes was changed from p.CMV-1 to p.CMV-2 which overlapped to some degree with the sequence of p.CMV-1. The sequence recognized by the biotinylated, 5'-arm of the looped probes overlaps with the sequence recognized by the non-biotinylated, 3'-arm of the first generation single molecule probes. The non-biotinylated, 3'-arm of the looped probes recognizes the sequence that lies immediately downstream to the region recognized by the biotinylated arm of this probe. In the looped probes the two arms had the same Tm and were identical in all six variants.

TABLE 7

Looped probes

| No. | Sequence 5'–3' | SEQ ID NO: |
|---|---|---|
| 1 | b-CAGCATCACACTAGTCTCTACTCGAGCAAAAAAAAAAAAAAAAAA AAAAACACTCGAGCGCTCTAAGACATAGCAGCA | 30 |
| 2 | b-AGCATCACACTAGTCTCTACACACACATCGAGCATTCGACACAC ACACGCTCTAAGACATAGCAGCA | 31 |
| 3 | b-CAGCATCACACTAGTCTCTACACTCGAGCACACAAAAAAAAAAA ACACACTCGAGCACGCTCTAAGACATAGCAGCA | 32 |
| 4 | b-CAGCATCACACTAGTCTCTACTCGAGCACACAAAAAAAAAAA ACACACACTCGAGCGCTCTAAGACATAGCAGCA | 33 |
| 5 | b-CAGCATCACACTAGTCTCTACACACCTCGAGCAAAAAAAAAAAA AAAAAAAAAACACTCGAGACACACGCTCTAAGACATAGCAGCA | 34 |
| 6 | b-CAGCATCACACTAGTCTCTACACTCGAGCACAAAAAAAAAAA AAAAACACACTCGAGCACGCTCTAAGACATAGCAGCA | 35 | b = 5' biotinylation.

To test the efficiency of hybridization of a looped probe to double stranded-CMV-DNA, different lengths fragments of CMV-DNA were employed in separate hybridization reactions.

Approximately 1 pm of loop 3 (Table 7) and 500 fm of a 263 bp double stranded CMV-DNA fragment were added to a 12-well row of a 96-well plate. One pm of the loop 3 probe and 500 fm of a 35 bp double stranded CMV-DNA fragment were added to another 12-well row of the same plate. The hybridization assay was conducted as described hereinabove, with the exception that 100 ng/µl of tRNA was added as a carrier. Reactions were covered with mineral oil and the plates were heated to 95° C. for 10 minutes to allow strand separation. The plate was then transferred to a temperature gradient block in which each column of the plate was incubated at different temperature, ranging from 44° C. to 66° C., at 2° C. increments. Following incubation in the temperature gradient block, 10 µl aliquots of each sample were analyzed by a 12% native polyacrylamide gel. Biotinylated fragments were visualized as previously described in Example 1. The results as shown in FIGS. 8a–b.

At the range of temperatures tested (44° C. to 66° C.), no hybridization with the 263 bp double stranded CMV fragment was observed (FIG. 8b), whereas efficient hybridization of the probe was observed with the 35 bp double stranded CMV-DNA fragment at temperatures up to 58° C. (FIG. 8a). These results suggest that target length-dependent reannealing may affect probe hybridization efficiency at high temperatures. To overcome reannealing of the target DNA, higher probe concentration and lower reaction temperatures should be employed. However, as is shown in the next experiment, such problems are traversed when a single stranded target DNA template is used.

The efficiency of hybridization of the loop 2 probe (Table 2) to either a single stranded DNA fragment or a double stranded DNA fragment was also examined. The results are presented in FIGS. 9a–b.

Approximately 1 pm of looped probe 2 and 500 fm of either a double stranded (FIG. 9a) or a single stranded (FIG. 9b) synthetic CMV-DNA fragment (syn.CMV-2st.ds or antisense CMV-2.st, respectively) were incubated in 200 mM NaCl in a final volume of 25 µl. The single stranded CMV-DNA preparation antisense CMV-2.st) is a synthetic, non-biotinylated, antisense strand that perfectly matches the size of the target-specific arms of the loop 2 probe. The double stranded CMV-DNA preparation (syn.CMV-2st.ds), is a 1:1 mixture of this antisense strand with a biotinylated sense strand of the same CMV-DNA sequence (sense CMV-2.st). The following hybridization conditions were employed: 1 h at 44° C. (lane 1); 1 h at 44° C. followed by 10 minutes at 95° C. (lane 2); 1 h at 44° C. followed by 10 minutes at 95° C. and 1 h at 68° C. (lane 3); 1 h at 68° C. (lane 4). As can be seen from FIGS. 9a–b, when the looped probe was incubated only with antisense CMV-2.st strand (FIG. 9b), the hybrid was stable at both 44° C. and 68° C., and could reform at 68° C., following a 10 minute heating at 95° C. (lane 3). In the presence of the complementary strand of the target DNA (sense CMV-2.st, FIG. 9a, the loop-antisense hybrid formed at 44° C. (lane 1) and remained stable following 10 minutes incubation at 95° C. (lane 2). However, when prolonged incubation times at 68° C. were exercised, no stable hybrid was formed (lanes 3 and 4). This in spite of the fact that the probe was present in a 20-fold excess over the double stranded target DNA. Thus, it was concluded from these results that at a given concentration ratio between a target DNA and a probe, a lower reaction temperature is required to enable the looped probe to efficiently hybridize with the target DNA in the presence of both strands.

To further analyze the efficiency of hybridization of looped probes to template DNA the extent of probe hybridization and cleavage was analyzed at various single stranded template DNA concentrations. The results are shown in FIG. 10a–c.

This assay consisted of two identical sets of seven tubes, each tube containing 500 fm of the loop 5 probe (Table 7) and decreasing amounts of a single stranded 35 bp CMV-DNA fragment (antisense CMV-2.st) in a final volume of 25 µl. The molar ratio between antisense CMV-2.st and the probe was 1;1, 1;4, 1:10, 1:40, 1:100, 1:400 in tubes 1 to 6, respectively. No CMV-DNA was added to tube number 7. The assay was conducted in the presence of 100 ng/µl tRNA as a carrier, at pH=8.5 and 200 mM NaCl. The tubes were incubated at 53° C. to allow probe-DNA hybridization. From one set of tubes, 10 µl aliquots of each sample were analyzed by a 12% polyacrylamide native gel (FIG. 10a). At the end of the hybridization step, TaqI was added to each tube of the second set of tubes, to a final concentration of 0.15 u/µl and the samples were incubated for 2 hours. A 10 µl aliquot from each sample of the second set of tubes was analyzed on a 15% polyacrylamide denaturing gel containing 7M urea (FIG. 10b), so as to detect the single stranded biotinylated fragments. The same samples were also analyzed by a 12% native gel, to detect both double stranded and single stranded fragments (FIG. 10c).

As shown in FIGS. 10a–c, CMV-dependent probe cleavage can be detected with as little as 50 fm of DNA. Furthermore, the efficiency of probe cleavage was not reduced upon 4 or 10-fold reduction in hybrid concentration, suggesting the presence of probe amplification. This conclusion is further substantiated, when the same reaction mixes are loaded on a native 12% acrylamide gel, as shown in FIG. 10c. Under these conditions, cleavage products exhibiting lower gel mobility were detected. This result suggests that the cleaved probe products stay attached to the CMV-DNA. However, in the presence of high free-probe concentrations, the cleaved probe products hybridized to the CMV-DNA are replaced by the intact probe, indicating that recycling of the target DNA indeed occurs. Thus, this experiment proves that template recycling and signal amplification can be achieved using looped probes synthesized according to the teachings of the present invention.

Looped probe variants: Variants of the looped probes included changes to the stem and loop regions so as to reduce CMV-DNA independent cleavage and to allow better recognition, association and stem cleavage by the restriction enzymes utilized. Several approaches can be undertaken in order to reduce CMV-DNA independent cleavage: A loop region can be generated which assumes the loop and stem configuration in the presence of target DNA and folds to block the restriction site in the absence of template DNA. The stem region can be shortened to four bp only, thus reducing template independent stem formation. Several approaches can be undertaken in order to enhance cleavage efficiency: The base portion of the pseudo double helix can be closed below the restriction site by a real duplex (two bp long), to form a pseudo-duplex/bulge loop, 10 bp in length. The restriction site can be placed in between two pseudo-duplex/bulge loops, each seven bp long. A nucleotide of the restriction site can be modified on one strand only, in which case loss of stability caused by this modification can be compensated for by increasing the stem length. Finally, CMV-DNA dependent cleavage may be enhanced by the addition of a real duplex (three bp long) on each side of the restriction site, and replacement of the poly A loop with a pseudo duplex loop.

Blocked probes: The blocked probes are characterized by the ability of the unhybridized probe to fold so as to form an intrinsic, non-restriction site containing, duplex structure (SEQ ID NOs:36–37) (see FIG. 2). A blocked probe is stable due to the high Tm of the intramolecular interactions of this duplex structure. When so folded, the probe may hybridize to a target molecule, however, only part of the non-biotinylated arm will be available for this hybridization, and therefore such a target-probe hybrid would to unstable. Thus, a stable hybrid state must be favored energetically such that the driving force for a configurational change of this probe would be a reduction in its energy state. For the full-length arm to be available for hybridization with the target DNA, the non-restriction site containing, duplex structure, should dissociate. Such a dissociation would cause a temporary loss of stability of the probe (e.g., Tm shift form Tm=52° C./69° C. to Tm=41° C./64° C., respectively), however, hybridization with a target should be able to compensate for this loss of stability.

Example 7

Bivalent Probes (BIV):

As shown in FIG. 2, the bivalent probes are paired probes designed to co-recognize two target DNA sequences. Each oligonucleotide member of the pair has a stem sequence flanked by one target recognition arm on each end. Each oligonucleotide member is biotinylated on its 5'-end. This probe design aims at further stabilizing stem formation and at increasing the dependency of stem formation on the presence of the target DNA. The BIV probes may be used to detect either two identical single strand sequences (BIV1), two complementary strands of a given double strand sequence (BIV2), two regions of the same polynucleotide or two non-related single strand sequences (BIV3). A BIV 3 probe targeting either an antisense/sense CMV-2 mixture, CMV-6 (SEQ ID NO:38) or the p.CMV-263.ds sequence was designed and synthesized. The probe comprises 5'-b-CAGCATCACACTAGTCTCAATTC-GAAGCGGATGACCATG TACGG-3' (SEQ ID NO:39) and 5'-b-CACTAGTGACGCTTGTATCGCTTCG AATTCTCTAAGACATAGCAGCA-3' (SEQ ID NO:40).

Co-detection of two identical single-strands (BIV1): For detection of two identical single strands each member of the bivalent probe includes one arm which recognizes the 3'-end of a target sequence and one arm which recognizes the 5'-end of the target sequence. Since the BIV1 probes twice as many target molecules are needed for a stable stem to be formed, the sensitivity of the assay may be reduced. However, since both members of the pair are labeled, the cleavage of each pair will produce two labeled cleavage products, thus compensating for the increased need for target molecules.

Co-detection of two complementary strands of a given double strand sequence (BIV2): For detection of two complementary strands of a double stranded sequence, the 5'-arm of one member of the bivalent probe and the 3'-arm of the second member are designed so as to hybridize with the antisense strand of a target sequence, while the other arms of both members are designed to recognize the sense strand of the same target DNA. The advantage of this design over the paired probes described above is that the BIV2 probes may complete with the reannealing reaction of a double stranded target DNA, which results in an increased sensitivity of the assay.

Co-detection of two-non-related single strands (BIV3): BIV3 allows the detection of two independent single stranded sequences, and as such presents two new detection options. First, two non-adjacent sequences of the same target DNA may be co-detected, thus increasing the specificity of the assay and reducing false positives without the need for an increase in DNA concentration. Alternatively, one probe-pair can be used to recognize two independent target molecules. For this purpose, the 5'-arm of one member of the bivalent probe and the 3'-arm of the second member are designed so as to recognize one target, while the other arms of both members are designed so as to recognize a second, independent target DNA.

Example 8

Fluorescent Detection Strategies

As detailed hereinabove, the detection of a probe and of restriction products thereof was effected using biotinylated probes and colorimetric methods. Although this method of detection is suitable for detecting various hybridization configuration when combined with gel separation, it detects both the hydridized and non-hybridized probe and as such is not suitable for diagnostic purposes. To provide suitable diagnostic detection several methods can be used.

For example, a fluorescent reporter dye and a quencher group which flank the restriction site of the same strand can be used. The quencher is capable of capturing the energy emitted by the fluorescent group, and as such, as long as the two groups are close enough to each other no fluorescence will be emitted when the fluorescent group is excited. In order to allow intra-probe hybridization and formation of a double stranded stem in the presence of the target DNA, the fluorescent reporter dye and the quencher group can be positioned on the ends of the stem region, on the sequence between first and third regions in both single and bi-molecular probes and on the loop in single molecule probes or on the end of the stem region in bi-molecular probes. At these positions the effect of the dyes on hybridization is minimized (see FIGS. 3a–b). For efficient cleavage of the stem by a restriction endonuclease a spacer of 4–18 bases is needed between the fluorescent reporter dye and a quencher group, depending on the restriction enzyme being used. Upon enzymatic cleavage, the fluorescent reporter dye and a quencher group separate from each other and become dispersed in solution. As a consequence, the energy transfer from the fluorescent group to the quencher does not exist, and fluorescence may be detected.

Since fluorescence may be detected as the reaction proceeds, a realtime measurement of the amplification is possible. The intensity and rate of fluorescence increase, may allow estimation of the number of target molecules present in the mixture and the rate of amplification. This in turn implies that probes synthesized according to the teachings of the present invention can also be used as complementary reagent for real-time follow up of PCR assays, in which target detection is typically performed only after amplification has been completed. Furthermore, since the signals generated by these probes is self amplified, the probes may increase the sensitivity of a PCR assay and allow reduction in the number of thermal cycles required for target detection.

Many fluorescent/quencher combinations may be utilized by the probes of the present invention. Combinations in which the donor is from the xanthene group of dyes, including fluoresceins, and the quencher is from the rhodamine group of dyes (6-FAM and TAMRA, for example) are commonly used in the art. Cy5 and ROX are another pair of dyes that can be used. Using this pair a 20-fold change in fluorescence in the presence of target can be experienced.

Non-fluorescent quenchers such as DABSYL and QSF-7 can also be used, these quenchers allow a higher degree of flexibility in choosing the fluorescent dyes. The choice of dye-pair requires that the quencher will absorb the energy of the fluorescent dye when the two are in close proximity. It is preferable that the increase in fluorescence upon dye separation would be as large as possible (3–20 fold increase in fluorescence was reported for various energy transfer systems). When only one fluorescent dye is used, a dye with the highest fluorescence intensity (usually having a broad emission spectrum) should be chosen. If two probes that carry the same fluorescent/quencher groups are designed for the detection of two distinct regions of the same target, sensitivity of the assay may be increased. Alternatively, two or more probes that are targeted to different targets can also be used providing that different combination of fluorescent/quencher dyes are utilized. However, in case when two or more fluorescent dyes are used, the sensitivity of the assay may be compromised in order to distinguish among the fluorescence of the various dyes. This may be done by detection of narrower emission spectrums, in which the fluorescence of the various dyes would not overlap.

Example 9

Fluorescent Detection of Target DNA

A 25 or 250 fm sample of a 50-bp segment derived from CMV (p.CMV-1) was used as a target DNA template. The sequence of the DNA template was as follows: 5'-TCAGGCTTGGTTATCAGAGGCCGCT TGGCCAG-CATCACA CTAGTCTCCTC-3' (SEQ ID NO:41).

A paired probe was covalently labeled with a 6-FAM fluorescent group on the 5'-end of the oligonucleotide member that corresponds to the 3'-region of the target sequence. 10 bases downstream of the FAM group, a QSY-7 quencher group was covalently attached to a thymidine residue at the base of the stem of the paired probe 2 (sequence in Table 2).

The assay was conducted in the presence of 200 mM NaCl, 10 mM Tris pH-7.8, and 10 mM $MgCl_2$, at 62° C., in a final volume of 25 µl.

The samples were boiled for 5 minutes to allow strand separation, and then cooled to 62° C., for 15 minutes to allow hybridization of the probe to its complementary sequence of the target DNA. Following probe hybridization TaqI endonuclease was added in a final concentration of 0.17 u/µl to allow probe digestion. Following a 2 h incubation period, the reactions were stopped with 10 mM EDTA.

FAM fluorescence was measured using a fluorometer having xenon arc lamp and grating monochromators for controlling excitation and emission wavelengths (496 nm and 516 nm, respectively). Samples taken prior to the addition of the enzymes were used as a blank. The difference in fluorescence in the presence of CMV-DNA and in its absence, indicated CMV-dependent cleavage of the probe, and thus, the amount of CMV-DNA may also be estimated.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference in the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of detecting a presence or an absence of a target nucleic acid sequence in a sample, the method comprising the steps of:
   (a) contacting the sample with an oligonucleotide system under hybridization conditions so as to form a reaction mixture, said oligonucleotide system including an anchor oligonucleotide and an amplifier oligonucleotide, each of said anchor and said amplifier oligonucleotides includes a first region complementary with the target nucleic acid sequence, each of said anchor and said amplifier oligonucleotides further including a second region, said second regions of said anchor and said amplifier oligonucleotides being at least partially complementary and thus capable of forming a duplex structure including a nucleic acid cleaving agent recognition sequence following hybridization of said first regions of said anchor and said amplifier oligonucleotides with the target nucleic acid sequence, said anchor and said amplifier oligonucleotides are selected such that when hybridized with the target nucleic acid sequence in a presence of a nucleic acid cleaving agent recognizing said nucleic acid cleaving agent recognition sequence, only said amplifier oligonucleotide is cleavable by said nucleic acid cleaving agent, wherein cleavage of said amplifier oligonucleotide leads to dissociation of said amplifier oligonucleotide from the target nucleic acid sequence while said anchor oligonucleotide remains hybridized to, and does not dissociate from, the target nucleic acid sequence to form a stabilized anchor oligonucleotide-target nucleic acid sequence hybrid, thereby allowing a second and uncleaved amplifier oligonucleotide to hybridize with said anchor oligonucleotide-target nucleic acid sequence hybrid, thus enabling recycling of said anchor oligonucleotide-target nucleic acid sequence hybrid with respect to said amplifier oligonucleotide;
   (b) adding said nucleic acid cleaving agent to said reaction mixture under predetermined reaction conditions, such that, if the target nucleic acid sequence is present in the sample, said nucleic acid cleaving agent recognition sequence is cleaved by said nucleic acid cleaving agent; and
   (c) monitoring cleavage of said nucleic acid cleaving agent recognition sequence by said nucleic acid cleaving agent;
   wherein cleavage of said nucleic acid cleaving agent recognition sequence by said nucleic acid cleaving agent indicates hybridization of the oligonucleotide system to the target nucleic acid sequence and therefore the presence of the target nucleic acid in the sample.

2. The method of claim 1, wherein under said hybridization conditions said first region said amplifier oligonucleotide is stably hybridizable with said target nucleic acid sequence only if said first region of said anchor oligonucleotide is stably hybridizable with said nucleic acid target sequence.

3. The method of claim 1, wherein at least one nucleotide or internucleotidic bond of said anchor oligonucleotide which forms a part of said nucleic acid cleaving agent recognition sequence includes a modification selected so as to prevent cleavage of said anchor oligonucleotide by said nucleic acid cleaving agent.

4. The method of claim 1, wherein said duplex structure is formed in part by self annealing of a portion of said second region of said amplifier oligonucleotide.

5. The method of claim 1, wherein a sequence of said first region of said anchor oligonucleotide is selected such that said anchor oligonucleotide remains annealed with said target nucleic acid sequence under said predetermined reaction conditions, whereas said sequence of said first region of said amplifier oligonucleotide is selected such that said amplifier oligonucleotide dissociates from said target nucleic acid sequence under said predetermined reaction conditions, following cleavage of said nucleic acid cleaving agent recognition sequence by said nucleic acid cleaving agent.

6. The method of claim 5, wherein a Tm of said first region of said anchor oligonucleotide is at least 10° C. higher than said Tm of said first region of said amplifier oligonucleotide.

* * * * *